United States Patent [19]
Chambers et al.

[11] Patent Number: 5,973,156
[45] Date of Patent: Oct. 26, 1999

[54] PIPERIDINE AND TETRAHYDROPYRIDINE DERIVATIVES

[75] Inventors: Mark Stuart Chambers, Ware; Sarah Christine Hobbs, Great Dunmow; Tamara Ladduwahetty, London; Angus Murray MacLeod, Bishops Stortford; Kevin John Merchant, Stevenage, all of United Kingdom

[73] Assignee: Merck Sharp & Dome Ltd., Hoddesdon, United Kingdom

[21] Appl. No.: 09/068,723

[22] PCT Filed: Nov. 14, 1996

[86] PCT No.: PCT/GB96/02795

§ 371 Date: May 13, 1998

§ 102(e) Date: May 13, 1998

[87] PCT Pub. No.: WO97/19073

PCT Pub. Date: May 29, 1997

[30] Foreign Application Priority Data

Nov. 17, 1995 [GB] United Kingdom .................... 9523583

[51] Int. Cl.$^6$ ..................... C07D 401/14; C07D 413/14; C07D 409/14; A61K 31/445
[52] U.S. Cl. ............................................ 546/201; 514/323
[58] Field of Search ............................................... 546/201

[56] References Cited

U.S. PATENT DOCUMENTS 5,451,588   9/1995   Baker et al. ............................ 514/323

FOREIGN PATENT DOCUMENTS

| 0200322 | 5/1986 | European Pat. Off. . |
|---|---|---|
| 0354777 | 2/1990 | European Pat. Off. . |
| 0 438 230 A2 | 7/1991 | European Pat. Off. . |
| 92/00070 | 1/1992 | WIPO . |
| 92/13856 | 8/1992 | WIPO . |
| 93/34116 | 12/1993 | WIPO . |
| 94/02477 | 2/1994 | WIPO . |
| 95/21166 | 8/1995 | WIPO . |
| 95/32196 | 11/1995 | WIPO . |

*Primary Examiner*—Alan L. Rotman
*Assistant Examiner*—Rita Desai
*Attorney, Agent, or Firm*—Philippe L. Durette; Melvin Winokur

[57] ABSTRACT

A class of substituted piperidine and tetrahydropyridine derivatives, linked through the 4-position thereof via an alkylene chain to a fused bicyclic heteroaromatic moiety such as indolyl, and further substituted at the 1-position by an optionally substituted alkyl, alkenyl, alkynyl, cycloalkyl-alkyl, aryl-alkyl or heteroaryl-alkyl moiety, are selective agonists of 5-HT$_1$-like receptors, being potent agonists of the human 5-HT$_{1D\alpha}$ receptor subtype whilst processing at least a 10-fold selective affinity for the 5-HT$_{1D\alpha}$ receptor subtype relative to the 5-HT$_{1D\beta}$ subtype; they are therefore useful in the treatment and/or prevention of clinical conditions, in particular migraine and associated disorders, for which a subtype-selective agonist of 5-HT$_{1D}$ receptors is indicated, whilst eliciting fewer side-effects, notably adverse cardiovascular events, than those associated with non-subtype-selective 5-HT$_{1D}$ receptor agonists.

12 Claims, No Drawings

PIPERIDINE AND TETRAHYDROPYRIDINE DERIVATIVES

CROSS-REFERENCE

This application is a 371 of PCT/GB96/02795 filed on Nov. 14, 1996.

The present invention relates to a class of substituted piperidine and tetrahydropyridine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., The Lancet, 1988, Vol. 1, 1309–11; and W. Feniuk and P. P. A. Humphrey, Drug Development Research, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., Br. Med. J., 1992, 304, 1415; J. P. Ottervanger et al., The Lancet, 1993, 341, 861–2; and D. N. Bateman, The Lancet, 1993, 341, 221–4). Since sumatriptan barely discriminates between the human 5-HT$_{1D\alpha}$ and 5-HT$_{1D\beta}$ receptor subtypes (cf. WO-A-91/17174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf G. W. Rebeck et al., Proc. Natl. Acad. Sci. USA, 1994, 91, 3666–9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the substituted piperidine and tetrahydropyridine derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the substituted piperazine moiety with a differently substituted piperidine or tetrahydropyridine moiety.

WO-A-91/18897 describes a class of tryptamine derivatives substituted by various five-membered rings, which are stated to be specific to a particular type of "5-HT$_1$-like" receptor and thus to be effective agents for the treatment of clinical conditions, particularly migraine, requiring this activity. A further class of tryptamine derivatives with alleged anti-migraine activity is disclosed in WO-A-94/02460. However, neither WO-A-91/18897 nor WO-A-94/02460 discloses or suggests the substituted piperidine and tetrahydropyridine derivatives provided by the present invention.

Moreover, nowhere in the prior art mentioned above is there any disclosure of a subtype-selective 5-HT$_{1D}$ receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

The compounds according to the present invention are subtype-selective 5-HT$_{1D}$ receptor agonists having a human 5-HT$_{1D\alpha}$ receptor binding affinity (IC$_{50}$) below 100 nM, typically below 50 nM, suitably below 10 nM and preferably below 1 nM; and at least a 10-fold selective affinity, typically at least a 50-fold selective affinity and preferably at least a 100-fold selective affinity, for the human 5-HT$_{1D\alpha}$ receptor subtype relative to the 5-HT$_{1D\beta}$ subtype. Moreover, the compounds in accordance with this invention possess interesting properties in terms of their efficacy and/or bioavailability.

The present invention provides a compound of formula I, or a salt or prodrug thereof:

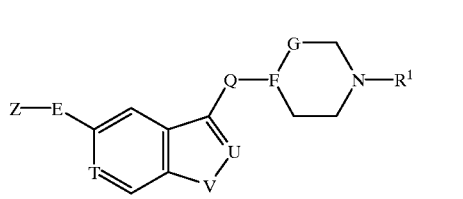

(I)

wherein

Z represents hydrogen, halogen, cyano, nitro, trifluoromethyl, —OR$^5$, —OCOR$^5$, —OCONR$^5$R$^6$, —OCH$_2$CN, —OCH$_2$CONR$^5$R$^6$, —SR$^5$, —SOR$^5$, —SO$_2$R$^5$, —SO$_2$NR$^5$R$^6$, —NR$^5$R$^6$, —NR$^5$COR$^6$, —NR$^5$CO$_2$R$^6$, —NR$^5$SO$_2$R$^6$, —COR$^5$, —CO$_2$R$^5$, —CONR$^5$R$^6$, or a group of formula (Za), (Zb), (Zc) or (Zd):

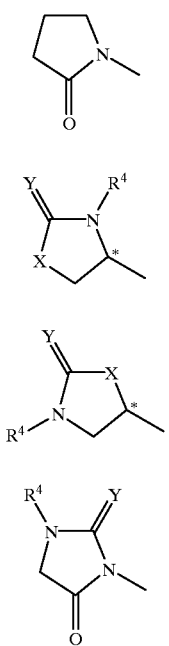

in which the asterisk * denotes a chiral centre; or

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

X represents oxygen, sulphur, —NH— or methylene;

Y represents oxygen or sulphur;

E represents a chemical bond or a straight or branched alkylene chain containing from 1 to 4 carbon atoms;

Q represents a straight or branched alkylene chain containing from 1 to 6 carbon atoms, optionally substituted in any position by one or more substituents selected from fluoro and hydroxy, or by an oxo moiety;

T represents nitrogen or CH;

U represents nitrogen or C—$R^2$;

V represents oxygen, sulphur or N—$R^3$;

—F—G— represents —CM—$CH_2$— or —C=CH—;

M represents hydrogen, halogen or $C_{1-6}$ alkoxy;

$R^1$ represents $C_{3-6}$ alkyl, $C_{3-6}$ alkenyl, $C_{3-6}$ alkynyl, $C_{3-7}$ cycloalkyl($C_{1-6}$)alkyl, aryl($C_{1-6}$)alkyl or heteroaryl($C_{1-6}$)alkyl, any of which groups may be optionally substituted;

$R^2$, $R^3$ and $R^4$ independently represent hydrogen or $C_{1-6}$ alkyl; and $R^5$ and $R^6$ independently represent hydrogen, $C_{1-6}$ alkyl, trifluoromethyl, phenyl, methylphenyl, or an optionally substituted aryl($C_{1-6}$)alkyl or heteroaryl($C_{1-6}$)alkyl group; or $R^5$ and $R^6$, when linked through a nitrogen atom, together represent the residue of an optionally substituted azetidine, pyrrolidine, piperidine, morpholine or piperazine ring.

The present invention also provides compounds of formula I as defined above, and salts and prodrugs thereof, wherein Q represents a straight or branched alkylene chain containing from 1 to 6 carbon atoms, optionally substituted in any position by one or more substituents selected from fluoro and hydroxy.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano and trifluoromethyl.

The group $R^1$ may be optionally substituted by one or more substituents, as also may the groups $R^5$ or $R^6$ where these represent aryl($C_{1-6}$)alkyl or heteroaryl($C_{1-6}$)alkyl. Where $R^1$, $R^5$ or $R^6$ represents aryl($C_{1-6}$)alkyl or heteroaryl($C_{1-6}$)alkyl, any optional substitution will suitably be on the aryl or heteroaryl moiety thereof, although substitution on the alkyl moiety thereof is an alternative possibility. Examples of optional substituents thereon include halogen, cyano, trifluoromethyl, triazolyl, tetrazolyl, $C_{1-6}$ alkyltetrazolyl, hydroxy, keto, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl, arylsulphonyl, amino, $C_{1-6}$ alkylamino, di($C_{1-6}$)alkylamino, di($C_{1-6}$)alkylaminomethyl, $C_{2-6}$ alkylcarbonylamino, arylcarbonylamino, $C_{2-6}$ alkoxycarbonylamino, N—($C_{1-6}$) alkyl—N—($C_{2-6}$)alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$) alkylaminocarbonylamino, mono- or diarylaminocarbonylamino, pyrrolidinylcarbonylamino, piperidinylcarbonylamino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$) alkylaminosulphonyl, aminosulphonylmethyl, $C_{1-6}$ alkylaminosulphonylmethyl and di($C_{1-6}$) alkylaminosulphonylmethyl.

When $R^5$ and $R^6$, when linked through a nitrogen atom, together represent the residue of an azetidine, pyrrolidine, piperidine, morpholine or piperazine ring, this ring may be unsubstituted or substituted by one or more substituents. Examples of suitable substituents include $C_{1-6}$ alkyl, aryl ($C_{1-6}$)alkyl, $C_{1-6}$ alkoxy, $C_{2-6}$ alkoxycarbonyl and $C_{1-6}$ alkylaminocarbonyl. Typical substituents include methyl, benzyl, methoxy, methoxycarbonyl, ethoxycarbonyl and methylaminocarbonyl. In particular, where $R^5$ and $R^6$ together represent the residue of a piperazine ring, this ring is preferably substituted on the distal nitrogen atom by a $C_{2-6}$ alkoxycarbonyl moiety such as methoxycarbonyl or ethoxycarbonyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n1-propyl, isopropyl and tert-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl, dimethylallyl and butenyl groups.

The expression "$C_{2-6}$ alkynyl" as used herein refers to straight-chained and branched alkynyl groups containing from 2 to 6 carbon atoms. Typical examples include ethynyl and propargyl groups.

Typical $C_{3-7}$ cycloalkyl groups include cyclopropyl, cyclobutyl, cyclopentyl and cyclohexyl.

Typical C$_{3-7}$ cycloalkyl(C$_{1-6}$)alkyl groups include cyclopropylmethyl and cyclohexylmethyl.

Typical aryl groups include phenyl and naphthyl.

The expression "aryl(C$_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridinyl, quinolinyl, isoquinolinyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl(C$_{1-6}$)alkyl" as used herein includes furylmethyl, furylethyl, thienylmethyl, thienylethyl, thienylpropyl, oxazolylmethyl, oxazolylethyl, thiazolylmethyl, thiazolylethyl, thiazolylpropyl, pyrazolylpropyl, imidazolylmethyL, imidazolylethyl, imidazolylpropyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridinylpropyl, pyridazinylpropyl, pyrimidinylmethyl, pyrimidinylpropyl, pyrazinylmethyl, pyrazinylpropyl, quinolinylmethyl and isoquinolinylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. For example, the compounds of formula I above wherein Z represents a group of formula (Zb) or (Zc) have a chiral centre denoted by the asterisk *, which may accordingly be in the (R) or (S) configuration. It is to be understood that all such isomers and mixtures thereof in any proportion are encompassed within the scope of the present invention.

Where E and Q, which may be the same or different, represent straight or branched alkylene chains, these may be, for example, methylene, ethylene, 1-methylethylene, propylene, 2-methylpropylene or butylene. In addition, the alkylene chain Q may be substituted in any position by one or more substituents selected from fluoro and hydroxy giving rise, for example, to a 2-hydroxypropylene, 2-hydroxymethylpropylene, 2-fluoropropylene or 2-fluoromethyl-propylene chain Q. Moreover, Q may represent a 1-hydroxypropylene linkage or be substituted in any position by an oxo moiety giving rise, for example, to a 2-oxopropylene chain Q. Furthermore, E may represent a chemical bond such that the moiety Z is attached directly to the central fused bicyclic heteroaromatic ring system containing the variables T, U and V.

Suitably, E represents a chemical bond or a methylene linkage.

Representative alkylene chains for Q include propylene, butylene, 2-hydroxypropylene, 2-hydroxymethylpropylene, 2-fluoropropylene and 2-fluoromethyl-propylene, especially propylene.

The compound of formula I in accordance with the present invention is suitably an indole, benzofuran or benzthiophene derivative of formula IA, an indazole derivative of formula IB, or a pyrrolo[2,3-c]pyridine derivative of formula IC:

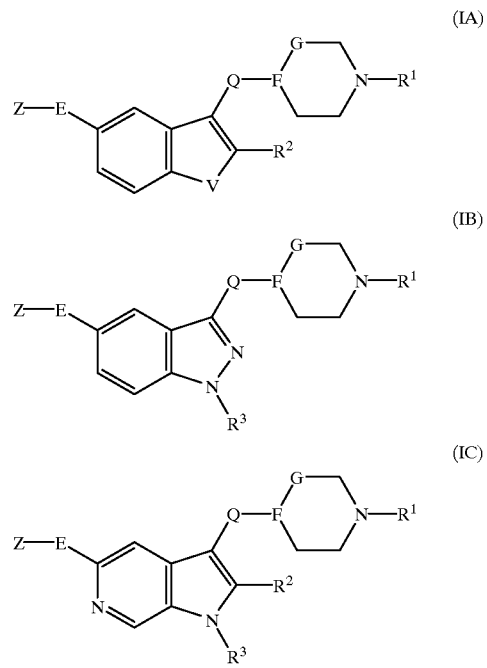

wherein Z, E, Q, V, F, G, R$^1$, R$^2$ and R$^3$ are as defined above. Preferably, the compounds according to the invention are indole or pyrrolo[2,3-c]pyridine derivatives of formula ID:

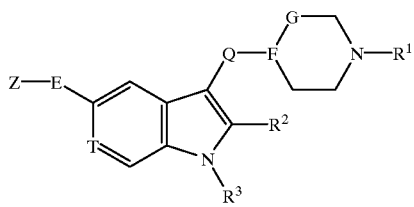

(ID)

wherein Z, E, Q, T, F, G, $R^1$, $R^2$ and $R^3$ are as defined above, in particular wherein $R^2$ and $R^3$ are both hydrogen.

Suitably, —F—G— represents —CM—CH$_2$—.

Suitably, M represents hydrogen, fluoro or methoxy, especially hydrogen or fluoro, and particularly hydrogen.

Suitable values for the substituent $R^1$ include 3,3-dimethylbutyl, allyl, dimethylallyl, butenyl, propargyl, cyclohexylmethyl, benzyl, phenylethyl, phenylpropyl, furylmethyl, thienylmethyl, thienylpropyl, thiazolylpropyl, pyrazolylpropyl, imidazolylmethyl, imidazolylpropyl, pyridinylmethyl, pyridinylpropyl, pyridazinylpropyl, pyrimidinylpropyl and pyrazinylpropyl, any of which groups may be optionally substituted. Selected values of $R^1$ include 3,3-dimethylbutyl, allyl, dimethylallyl, butenyl, propargyl, cyclohexylmethyl, benzyl, phenylethyl, phenylpropyl, furylmethyl, thienylmethyl, imidazolylmethyl and pyridinylmethyl, any of which groups may be optionally substituted. Typical substituents on the group $R^1$ include halogen, cyano, trifluoromethyl, triazolyl, tetrazolyl, $C_{1-6}$ alkyl-tetrazolyl, hydroxy, keto, $C_{1-6}$ alkoxy, amino, di($C_{1-6}$)alkylamino, di($C_{1-6}$)alkylaminomethyl, $C_{2-6}$ alkylcarbonylamino, $C_{2-6}$ alkoxycarbonylamino, N—($C_{1-6}$)alkyl—N—($C_{2-6}$)alkoxycarbonylamino, $C_{1-6}$ alkylsulphonylamino, aminocarbonylamino, aminocarbonyl, $C_{1-6}$ alkylaminocarbonyl, di($C_{1-6}$) alkylaminocarbonyl, aminosulphonyl and $C_{1-6}$ alkylaminosulphonylmethyl, especially halogen, trifluoromethyl, hydroxy, $C_{1-6}$ alkoxy, $C_{1-6}$ alkylaminocarbonyl and aminosulphonyl.

Particular values of $R^1$ include 3,3-dimethylbutyl, allyl, dimethylallyl, butenyl, propargyl, cyclohexylmethyl, benzyl, fluorobenzyl, difluorobenzyl, cyanobenzyl, tetrazolyl-benzyl, methyltetrazolyl-benzyl, methoxybenzyl, aminobenzyl, dimethylaminomethyl-benzyl, acetylaminobenzyl, aminocarbonyl-benzyl, methylaminocarbonyl-benzyl, dimethylaminocarbonyl-benzyl, aminosulphonyl-benzyl, phenylethyl, fluoro-phenylethyl, difluoro-phenylethyl, cyano-phenylethyl, trifluoromethyl-phenylethyl, triazolyl-phenylethyl, 2-hydroxy-1-phenylethyl, phenylcarbonylmethyl, amino-phenylethyl, dimethylamino-phenylethyl, acetylamino-phenylethyl, methoxycarbonylamino-phenylethyl, (N-methyl-N-methoxycarbonyl)amino-phenylethyl, aminocarbonylamino-phenylethyl, 2-phenylpropyl, 3-phenylpropyl, 2-(fluorophenyl)propyl, 2-(chlorophenyl)propyl, 2-(dichlorophenyl)propyl, 2-(trifluoromethylphenyl)propyl, 2-[(chloro)(trifluoromethyl)phenyl]propyl, 2-hydroxy-2-phenylpropyl, 2-(methoxyphenyl)propyl, 2-(aminosulphonylphenyl)propyl, furylmethyl, thienylmethyl, 2-(thienyl)propyl, 2-(thiazolyl)propyl, 2-(pyrazolyl)propyl, imidazolylmethyl, 2-(imidazolyl)propyl, pyridinylmethyl, 2-(pyridinyl)propyl, 2-(methoxypyridinyl)propyl, 2-(pyridazinyl)propyl, 2-(pyrimidinyl)propyl and 2-(pyrazinyl)propyl.

Particular values of $R^1$ include 3,3-dimethylbutyl, benzyl, methylaminocarbonyl-benzyl, phenylethyl, fluoro-phenylethyl, difluoro-phenylethyl, trifluoromethyl-phenylethyl, 2-hydroxy-1-phenylethyl, 2-phenylpropyl, 3-phenylpropyl, 2-(fluorophenyl)propyl, 2-(chlorophenyl)propyl, 2-(dichlorophenyl)propyl, 2-(trifluoromethylphenyl)propyl, 2-[(chloro)(trifluoromethyl)phenyl]propyl, 2-hydroxy-2-phenylpropyl, 2-(methoxyphenyl)propyl, 2-(aminosulphonylphenyl)propyl, 2-(thienyl)propyl, 2-(thiazolyl)propyl, 2-(pyrazolyl)propyl, 2-(imidazolyl)propyl, 2-(pyridinyl)propyl, 2-(methoxypyridinyl)propyl, 2-(pyridazinyl)propyl, 2-(pyrimidinyl)propyl and 2-(pyrazinyl)propyl.

An especial value of $R^1$ is 2-phenylpropyl.

Suitably, $R^2$ and $R^3$ independently represent hydrogen or methyl, especially hydrogen.

Suitably, $R^4$ represents hydrogen or methyl.

Suitably, $R^5$ and $R^6$ are independently selected from hydrogen, methyl, ethyl, n-propyl, isopropyl, n-butyl, tert-butyl, trifluoromethyl, phenyl, methylphenyl (especially 4-methylphenyl), benzyl and phenethyl.

Suitably, the substituent Z represents hydrogen, fluoro, cyano, hydroxy, methoxy, ethoxy, benzyloxy, methylaminocarbonyloxy, cyanomethoxy, aminocarbonyl-methoxy, methylsulphonyl, aminosulphonyl, N-methylamino-sulphonyl, N,N-dimethylamino-sulphonyl, amino, formylamino, acetylamino, trifluoromethyl-carbonylamino, benzyloxycarbonylamino, methyl-sulphonylamino, ethyl-sulphonylamino, methylphenyl-sulphonylamino, N-methyl-(N-methylsulphonyl)-amino, N-methyl-(N-ethylsulphonyl)-amino, N-methyl-(N-trifluoromethylsulphonyl)-amino, N-ethyl-(N-methylsulphonyl)-amino, N-benzyl-(N-methylsulphonyl)-amino, N-benzyl-(N-ethylsulphonyl)-amino, acetyl, methoxycarbonyl, ethoxycarbonyl, aminocarbonyl, methylaminocarbonyl, ethylaminocarbonyl, propylaminocarbonyl, butylaminocarbonyl, benzylaminocarbonyl or phenethyl-aminocarbonyl; or a group of formula (Za), (Zb), (Zc) or (Zd) as defined above; or an optionally substituted five-membered heteroaromatic ring as specified above.

In a particular embodiment, Z represents —SO$_2$NR$^5$R$^6$ in which $R^5$ and $R^6$ are as defined above. In a subset of this embodiment, $R^5$ and $R^6$ independently represent hydrogen or $C_{1-6}$ alkyl, especially hydrogen or methyl. Particular values of Z in this context include aminosulphonyl, N-methylamino-sulphonyl and N,N-dimethylamino-sulphonyl, especially N-methylamino-sulphonyl.

In another embodiment, Z represents a group of formula (Zb) in which $R^4$ is hydrogen or methyl. In a subset of this embodiment, X and Y both represent oxygen. In a particular aspect of this subset, the chiral centre denoted by the asterisk * is in the (S) configuration.

When the group Z represents an optionally substituted five-membered heteroaromatic ring, this is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, imidazole, 1,2,4-oxadiazole, 1,2,4-thiadiazole or 1,2,4-triazole ring, typically an imidazol-1-yl, 1,2,4-triazol-1-yl or 1,2,4-triazol-4-yl moiety, and in particular a 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino, especially ethyl.

A particular sub-class of compounds according to the invention is represented by the compounds of formula IIA, and salts and prodrugs thereof:

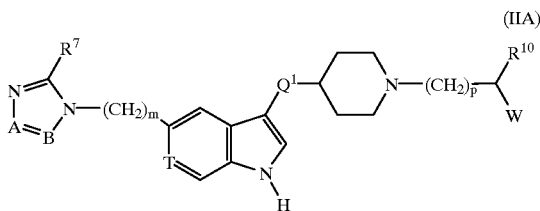

wherein m is zero, 1, 2 or 3, preferably zero or 1;

p is zero, 1 or 2;

$Q^1$ represents a straight or branched alkylene chain containing from 2 to 5 carbon atoms, optionally substituted in any position by one or more substituents selected from fluoro and hydroxy;

T represents nitrogen or CH;

A represents nitrogen or CH;

B represents nitrogen or C—$R^8$;

$R^7$ and $R^8$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;

W represents tert-butyl, cyclohexyl, phenyl, thienyl, thiazolyl, pyrazolyl, imidazolyl, pyridinyl, pyridazinyl, pyrimidinyl or pyridazinyl, any of which groups may be unsubstituted or substituted by one or more groups selected from halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di($C_{1-6}$)alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl and $C_{1-6}$ alkylaminosulphonylmethyl; and $R^{10}$ represents hydrogen, $C_{1-3}$ alkyl, hydroxy($C_{1-3}$)alkyl or $C_{1-6}$ alkylaminocarbonyl.

Examples of selected substituents on the moiety W include halogen (especially fluoro or chloro), trifluoromethyl, hydroxy, $C_{1-6}$ alkoxy (especially methoxy) and aminosulphonyl.

In a particular aspect, W represents tert-butyl, cyclohexyl or a group of formula (Wa), (Wb) or (Wc):

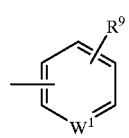

(Wa)

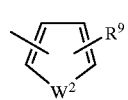

(Wb)

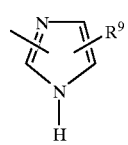

(Wc)

in which $W^1$ represents CH or nitrogen;

$W^2$ represents oxygen, sulphur, NH or N-methyl; and $R^9$ represents hydrogen, halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di($C_{1-6}$) alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl.

Suitably, $Q^1$ represents a straight or branched 3 or 4 carbon alkylene chain, optionally substituted in any position by one or more substituents selected from fluoro and hydroxy. Particular alkylene chains for $Q^1$ include propylene, butylene, 2-hydroxypropylene, 2-(hydroxymethyl)-propylene, 2-fluoropropylene and 2-(fluoromethyl)-propylene, especially propylene.

Particular values of $R^7$ and $R^8$ include hydrogen, methyl, ethyl, benzyl and amino, typically hydrogen or ethyl, and especially hydrogen.

Particular values of $R^9$ include hydrogen, fluoro, chloro, cyano, trifluoromethyl, triazolyl, tetrazolyl, methyl-tetrazolyl, methoxy, amino, dimethylaminomethyl, acetylamino, aminocarbonylamino, methylaminocarbonyl and aminosulphonyl, typically hydrogen, fluoro, chloro, trifluoromethyl, methoxy or aminosulphonyl, and especially hydrogen, fluoro or trifluoromethyl.

Particular values of $R^{10}$ include hydrogen, methyl, hydroxymethyl and methylaminocarbonyl, especially hydrogen or methyl.

Another sub-class of compounds according to the invention is represented by the compounds of formula IIB, and salts and prodrugs thereof:

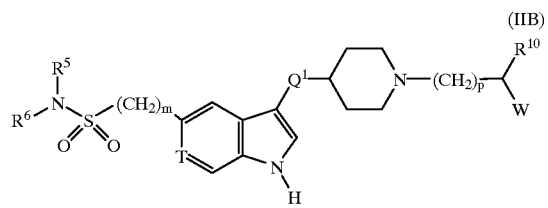

wherein m, p, $Q^1$, T, W and $R^{10}$ are as defined with reference to formula IIA above; and $R^5$ and $R^6$ are as defined with reference to formula I above.

Particular values of $R^5$ and $R^6$ in relation to formula IIB above include hydrogen and $C_{1-6}$ alkyl, especially hydrogen or methyl. Suitably, one of $R^5$ and $R^6$ represents hydrogen and the other represents hydrogen or methyl.

A further sub-class of compounds according to the invention is represented by the compounds of formula IIC, and salts and prodrugs thereof:

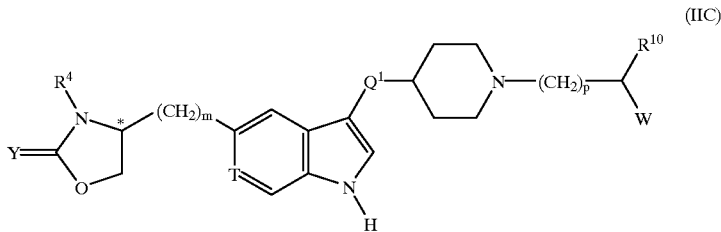

wherein the asterisk * denotes a chiral centre;
    m, p, $Q^1$, T, W and $R^{10}$ are as defined with reference to formula IIA above; and
    $R^4$ and Y are as defined with reference to formula I above.
Particular values of $R^4$ in relation to formula IIC include hydrogen and methyl, especially hydrogen.
Preferably, Y in formula IIC is oxygen.
Preferably, the chiral centre denoted by the asterisk * in formula IIC is in the (S) configuration.
Specific compounds within the scope of the present invention include:
1-benzyl-4-[3-(5-(1,2,4-triazol-4-yl)-1H-indol-3-yl)propyl]piperidine;
1-(3,3-dimethylbutyl)-4-[3-(5-(1,2,4-triazol-4-yl)-1H-indol-3-yl)propyl]piperidine;
1-(2-phenylethyl)-4-[3-(5-(1,2,4-triazol-4-yl)-1H-indol-3-yl)propyl]piperidine;
1-cyclohexylmethyl-4-[3-(5-(1,2,4-triazol-4-yl)-1H-indol-3-yl)propyl]piperidine;
1-(3-phenylpropyl)-4-[3-(5-(1,2,4-triazol-4-yl)-1H-indol-3-yl)propyl]piperidine;
1-[2-(3-fluorophenyl)ethyl]-4-[3-(5-(1,2,4-triazol-4-yl)-1H-indol-3-yl)propyl]piperidine;
1-[2-(4-trifluoromethylphenyl)ethyl]-4-[3-(5-(1,2,4-triazol-4-yl) -1H-indol-3-yl)propyl]piperidine;
1-[2-(3,4-difluorophenyl)ethyl]-4-[3-(5-(1,2,4-triazol-4-yl)-1H-indol-3-yl)propyl]piperidine;
N-methyl-2-phenyl-2-[4-(3-(5-(1,2,4-triazol-4-yl)-1H-indol-3-yl)propyl)piperidin-1-yl]acetamide;
1-(2-oxo-2-phenylethyl)-4-[3-(5-(1,2,4-triazol-4-yl)-1H-indol-3-yl)propyl]piperidine;
1-(2-phenylpropyl)-4-[3-(5-(1,2,4-triazol-4-yl)-1H-indol-3-yl)propyl]piperidine;
1-(2-hydroxy-1-phenylethyl)-4-[3-(5-(1,2,4-triazol-4-yl)-1H-indol-3-yl)propyl]piperidine;
1-[2-(2-fluorophenyl)ethyl]-4-[3-(5-(1,2,4-triazol-4-yl)-1H-indol-3-yl)propyl]piperidine;
4-[3-(5-(1,2,4-triazol-4-yl)-1H-indol-3-yl)propyl]-1-[2-(2-chlorophenyl)propyl]piperidine;
4-[3-(5-(1,2,4-triazol-4-yl)-1H-indol-3-yl)propyl]-1-[2-(2-trifluoromethylphenyl)propyl]piperidine;
4-[3-(5-(1,2,4-triazol-4-yl)-1H-indol-3-yl)propyl]-1-[2-(4-chlorophenyl)propyl]piperidine;
4-[3-(5-(1,2,4-triazol-4-yl)-1H-indol-3-yl)propyl]-1-[2-(4-methoxyphenyl)propyl]piperidine;
4-[3-(5-(1,2,4-triazol-4-yl)-1H-indol-3-yl)propyl]-[2-(2,6-dichlorophenyl)propyl]piperidine;
4-[3-(5-(1,2,4-triazol-4-yl)-1H-indol-3-yl)propyl]-1-[2-(3-methoxyphenyl)propyl]piperidine;
4-[3-(5-(1,2,4-triazol-4-yl)-1H-indol-3-yl)propyl]-1-[2-(2-methoxyphenyl)propyl]piperidine;
4-[3-(5-(1,2,4-triazol-4-yl)-1H-indol-3-yl)propyl]-1-[2-(3-chlorophenyl)propyl]piperidine;
4-[3-(5-(1,2,4-triazol-4-yl)-1H-indol-3-yl)propyl]-1-[2-(3-aminosulphonylphenyl)propyl]piperidine;
4-[3-(5-(1,2,4-triazol-4-yl)-1H-indol-3-yl)propyl]-1-[2-(pyrimidin-2-yl)propyl]piperidine;
4-[3-(5-(1,2,4-triazol-4-yl)-1H-indol-3-yl)propyl]-1-[2-(thiazol-2-yl)propyl]piperidine;
4-[3-(5-(1,2,4-triazol-4-yl)-1H-indol-3-yl)propyl]-1-[2-(pyrazin-2-yl)propyl]piperazine;
4-[3-(5-(1,2,4-triazol-4-yl)-1H-indol-3-yl)propyl]-1-[2-(imidazol-1-yl)propyl]piperazine;
4-[3-(5-(1,2,4-triazol-4-yl)-1H-indol-3-yl)propyl]-1-[2-(pyrazol-1-yl)propyl]piperidine;
4-[3-(5-(1,2,4-triazol-4-yl)-1H-indol-3-yl)propyl]-1-[2-(pyridin-2-yl)propyl]piperidine;
4-[3-(5-(1,2,4-triazol-4-yl)-1H-indol-3-yl)propyl]-1-[2-(pyridin-3-yl)propyl]piperidine;
4-[3-(5-(1,2,4-triazol-4-yl)-1H-indol-3-yl)propyl]-1-[2-(pyridin-4-yl)propyl]piperidine;
4-[3-(5-(1,2,4-triazol-4-yl)-1H-indol-3-yl)propyl]-1-[2-(pyridazin-3-yl)propyl]piperidine;
4-fluoro-4-[3-(5-(1,2,4-triazol-4-yl)-1H-indol-3-yl)propyl]-1-[2-(pyridin-3-yl)propyl]piperidine;
4-[3-(5-(1,2,4-triazol-4-yl)-1H-indol-3-yl)propyl]-1-[2-(thien-3-yl)propyl]piperidine;
4-[3-(5-(1,2,4-triazol-4-yl)-1H-indol-3-yl)propyl]-1-[2-(2-methoxypyridin-3-yl)propyl]piperidine;
4-[3-(5-(1,2,4-triazol-4-yl)-1H-indol-3-yl)propyl]-1-[2-(4-methoxypyridin-3-yl)propyl]piperidine;
4-[3-(5-(1,2,4-triazol-4-yl)-1H-indol-3-yl)propyl]-1-[(R)-2-(pyridin-3-yl)propyl]piperidine;
4-[3-(5-(1,2,4-triazol-4-yl)-1H-indol-3-yl)propyl]-1-[(S)-2-(pyridin-3-yl)propyl]piperidine;
4-[3-(5-(1,2,4-triazol-4-yl)-1H-indol-3-yl)propyl]-1-[(S)-(2-phenylpropyl)]piperidine;
4-[3-(5-(1,2,4-triazol-4-yl)-1H-indol-3-yl)propyl]-1-[(R)-2-phenylpropyl]piperidine;
4-[3-(5-(1,2,4-triazol-4-yl)-1H-indol-3-yl)propyl]-1-[2-(2-fluorophenyl)propyl]piperidine;
4-[3-(5-(1,2,4-triazol-4-yl)-1H-indol-3-yl)propyl]-1-[2-(3-fluorophenyl)propyl]piperidine;
4-[3-(5-(1,2,4-triazol-4-yl)-1H-indol-3-yl)propyl]-1-[2-(4-fluorophenyl)propyl]piperidine;
4-[3-(5-(1,2,4-triazol-4-yl)-1H-indol-3-yl)propyl]-1-[2-(2-chloro-5-(trifluoromethyl)phenyl)propyl]piperidine;
4-[3-(5-(1,2,4-triazol-4-yl)-1H-indol-3-yl)propyl]-1-[(S)-2-(4-fluorophenyl)propyl]piperidine;
4-[3-(5-(1,2,4-triazol-4-yl)-1H-indol-3-yl)propyl]-1-(2-hydroxy-2-phenylpropyl)piperidine;
4-[3-(5-(N-(methyl)aminosulphonylmethyl)-1H-indol-3-yl)propyl]-1-(2-phenylpropyl)piperidine;
4-[3-(5-(N-(methyl)aminosulphonylethyl)-1H-indol-3-yl)propyl]-1-(2-phenylpropyl)piperidine;
4-[3-(5-(2-ethylimidazol-1-yl)-1H-indol-3-yl)propyl]-1-(2-phenylpropyl)piperidine;
4-[3-(5-((S)-2-oxo-1,3-oxazolidin-4-ylmethyl)-1H-indol-3-yl)propyl]-1-(2-phenylpropyl)piperidine;
4-fluoro-4-[3-(5-(1,2,4-triazol-4-yl)-1H-indol-3-yl)propyl]-1-(2-phenylpropyl)piperidine;

4-[2-filuoro-3-(5-(1,2,4-triazol-4-yl)-1H-indol-3-yl)
propyl]-1-(2-phenylpropyl)piperidine;

4-[3-(5-(1,2,4-triazol-4-yl)-1H-indol-3-yl)-2-
hydroxypropyl]-1-(2-phenylpropyl)piperidine;

4-[3-(5-(1,2,4-triazol-4-yl)-1H-indol-3-yl)-2-oxopropyl]-1-
(2-phenylpropyl)piperidine;

4-[3-(5-(1,2,4-triazol-4-yl)-1H-indol-3-yl)-1-
hydroxypropyl]-1-(2-phenylpropyl)piperidine; and salts
and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention may be prepared by a process which comprises attachment of the $R^1$ moiety to a compound of formula III:

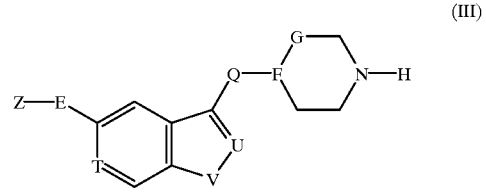

(III)

wherein Z, E, Q, T, U, V, F and G are as defined above; by conventional means including N-alkylation.

Attachment of the $R^1$ moiety to the compounds of formula III may conveniently be effected by standard alkylation techniques. One example thereof comprises treatment with an alkenyl halide such as 4-bromobut-1-ene, 4-bromo-2-methylbut-2-ene or allyl bromide, an alkynyl halide such as propargyl bromide, or an aryl($C_{1-6}$)alkyl or heteroaryl($C_{1-6}$)alkyl halide such as benzyl iodide, typically under basic conditions, e.g. sodium hydride in N,N-dimethylformamide, or potassium carbonate in isopropanol. Another example comprises treatment of the compound of formula III with an aryl($C_{1-6}$)alkyl or heteroaryl($C_{1-6}$)alkyl mesylate such as 2-(thiazol-2-yl)propyl methanesulphonate, ideally in the presence of a base such as sodium carbonate, in a suitable solvent such as 2-propanol, typically at the reflux temperature of the solvent. A further example, for the preparation of a compound of formula I in which $R^1$ is substituted with hydroxy, comprises treating the requisite compound of formula III with an epoxide derivative such as α-methylstyrene epoxide, typically in a solvent such as methanol in a sealed tube at an elevated temperature.

Alternatively, the $R^1$ moiety may conveniently be attached by reductive alkylation, which may be accomplished in a single step, or as a two-step procedure. The single-step approach suitably comprises treating the required compound of formula III as defined above with the appropriate aldehyde, e.g. benzaldehyde, pyridine carboxaldehyde, furfuraldehyde or thiophene carboxaldehyde, in the presence of a reducing agent such as sodium cyanoborohydride. In a typical two-step procedure, for the preparation of a compound of formula I wherein $R^1$ corresponds to a group of formula —$CH_2R^{11}$, a carboxylic acid derivative of formula $R^{11}$—$CO_2H$ is condensed with the required compound of formula III, suitably in the presence of 1-(3-dimethylaminopropyl)-3-ethylcarboduimide hydrochloride and 1-hydroxybenzotriazole hydrate, to afford a compound corresponding to formula I wherein $R^1$ represents —$COR^{11}$; the carbonyl group thereof can then be reduced, for example by treatment with diisobutylaluminium hydride, and the required compound of formula I thereby obtained.

The compounds of formula III above wherein T represents CH, U represents C—$R^2$ and V represents N—$R^3$, corresponding to the indole derivatives of formula ID as defined above wherein T represents CH and $R^1$ is hydrogen, may be prepared by a process which comprises reacting a compound of formula IV:

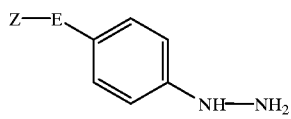

wherein Z and E are as defined above; with a compound of formula V, or a carbonyl-protected form thereof:

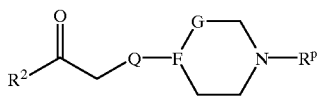

wherein Q, F, G and $R^2$ are as defined above, and $R^p$ represents an amino-protecting group; followed, where required, by N-alkylation by standard methods to introduce the moiety $R^3$; with subsequent removal of the amino-protecting group $R^p$.

The reaction between compounds IV and V, which is an example of the well-known Fischer indole synthesis, is suitably carried out by heating the reagents together under mildly acidic conditions, e.g. 4% sulphuric acid at reflux.

Suitable carbonyl-protected forms of the compounds of formula V include the dimethyl acetal or ketal derivatives.

The protecting group $R^p$ in the compounds of formula V is suitably a carbamoyl moiety such as tert-butoxycarbonyl (BOC), which can conveniently be removed as necessary by treatment under mildly acidic conditions. Indeed, the acidic conditions of the Fischer indole synthesis reaction will generally suffice to remove the BOC group.

The Fischer reaction between compounds IV and V may be carried out in a single step, or may proceed via an initial non-cyclising step at a lower temperature to give an intermediate of formula VI:

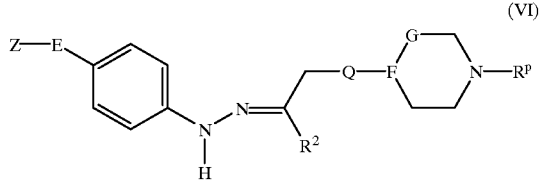

wherein Z, E, Q, F, G, $R^2$ and $R^p$ are as defined above; followed by cyclisation using a suitable reagent, e.g. a polyphosphate ester.

The compounds according to the invention wherein T represents CH, U represents C—$R^2$ and V represents N—$R^3$—i.e. the indole derivatives of formula ID as defined above wherein T represents CH—may alternatively be prepared by a process which comprises reacting a compound of formula IV as defined above with a compound of formula VII, or a carbonyl-protected form thereof:

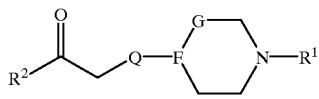

wherein Q, F, G, $R^1$ and $R^2$ are as defined above; under conditions analogous to those described above for the reaction between compounds IV and V; followed, where required, by N-alkylation by standard methods to introduce the moiety $R^3$.

As for the compounds of formula V, suitable carbonyl-protected forms of the compounds of formula VII include the dimethyl acetal or ketal derivatives. Where the alkylene chain Q is substituted by a hydroxy group, this group may condense with the carbonyl moiety in compounds V and VII, whereby the carbonyl moiety is protected in the form of a cyclic hemiacetal.

As with that between compounds IV and V, the Fischer reaction between compounds IV and VII may be carried out in a single step, or may proceed via an initial non-cyclising step at a lower temperature to give an intermediate of formula VIII:

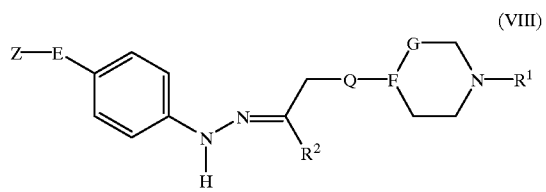

wherein Z, E, Q, F, G, $R^1$ and $R^2$ are as defined above; followed by cyclisation using a suitable reagent, e.g. a polyphosphate ester.

In a further procedure, the compounds of formula III above wherein T represents CH, U represents nitrogen and V represents N—$R^3$, corresponding to the indazole derivatives of formula IB as defined above wherein $R^1$ is hydrogen, may be prepared by a process which comprises cyclising a compound of formula IX:

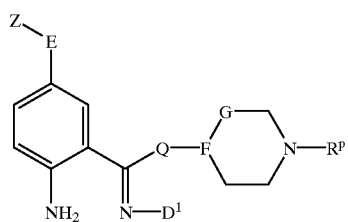

wherein Z, E, Q, F, G and $R^p$ are as defined above, and $D^1$ represents a readily displaceable group; followed, where required, by N-alkylation by standard methods to introduce the moiety $R^3$; with subsequent removal of the amino-protecting group $R^p$.

Similarly, the compounds of formula I wherein T represents CH, U represents nitrogen and V represents N—$R^3$—i.e. the indazole derivatives of formula IB as defined above—may be prepared by a process which comprises cyclising a compound of formula X:

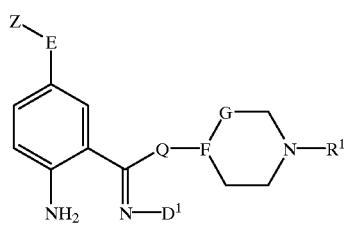

(X)

in which Z, E, Q, F, G, $R^1$ and $D^1$ are as defined above; followed, where required, by N-alkylation by standard methods to introduce the moiety $R^3$.

The cyclisation of compounds IX and X is conveniently achieved in a suitable organic solvent at an elevated temperature, for example in a mixture of m-xylene and 2,6-lutidine at a temperature in the region of 140° C.

The readily displaceable group $D^1$ in the compounds of formula IX and X suitably represents a $C_{1-4}$ alkanoyloxy group, preferably acetoxy. Where $D^1$ represents acetoxy, the desired compound of formula IX or X may be conveniently prepared by treating a carbonyl compound of formula XI:

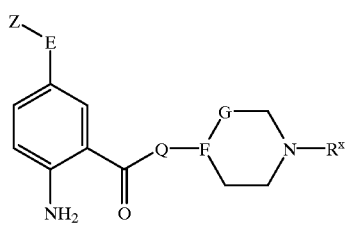

(XI)

wherein Z, E, Q, F and G are as defined above, and $R^x$ corresponds to the group $R^1$ as defined above, or $R^x$ represents an amino-protecting group as defined for $R^P$; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XI may conveniently be prepared by ozonolysis of the corresponding indole derivative of formula XII:

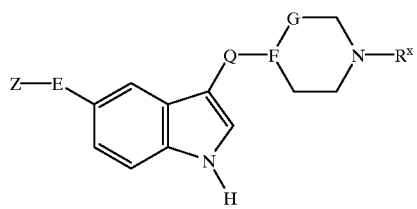

(XII)

wherein Z, E, Q, F, G and $R^x$ are as defined above; followed by a reductive work-up, advantageously using dimethylsulphide.

The indole derivatives of formula XII may be prepared by methods analogous to those described in the accompanying Examples, or by procedures well known from the art.

In a still further procedure, the compounds of formula III above wherein T represents CH, U represents C—$R^2$ and V represents oxygen or sulphur, corresponding to the benzofuran or benzthiophene derivatives of formula IA wherein V is oxygen or sulphur respectively and $R^1$ is hydrogen, may be prepared by a process which comprises cyclising a compound of formula XIII:

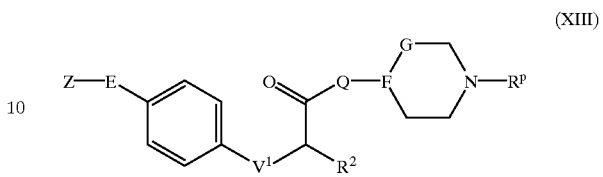

(XIII)

wherein Z, E, Q, F, G, $R^2$ and $R^P$ are as defined above, and $V^1$ represents oxygen or sulphur; followed by removal of the amino-protecting group $R^P$.

Similarly, the compounds of formula I wherein T represents CH, U represents C—$R^2$ and V represents oxygen or sulphur—i.e. the benzofuran or benzthiophene derivatives of formula IA above—may be prepared by a process which comprises cyclising a compound of formula XIV:

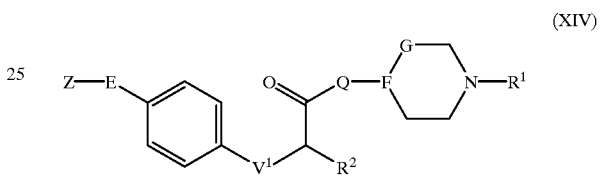

(XIV)

wherein Z, E, Q, F, G, $R^1$, $R^2$ and $V^1$ are as defined above.

The cyclisation of compounds XIII and XIV is conveniently effected by using polyphosphoric acid or a polyphosphate ester, advantageously at an elevated temperature.

The compounds of formula XIII and XIV may be prepared by reacting a compound of formula XV with a compound of formula XVI:

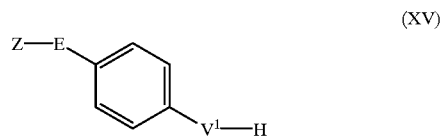

(XV)

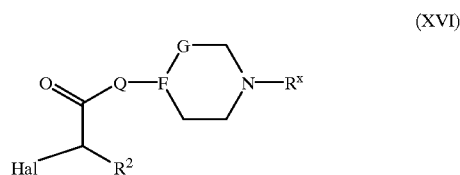

(XVI)

wherein Z, E, Q, F, G, $R^2$, $V^1$ and $R^x$ are as defined above, and Hal represents a halogen atom.

The reaction is conveniently effected in the presence of a base such as sodium hydroxide.

The hydroxy and mercapto derivatives of formula XV may be prepared by a variety of methods which will be readily apparent to those skilled in the art. One such method is described in EP-A-0497512.

The hydrazine derivatives of formula IV above may be prepared by methods analogous to those described in EP-A-0438230, EP-A-0497512, EP-A-0548813 and WO-A-91/18897.

Where they are not commercially available, the starting materials of formula V, VII and XVI may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by techniques known from the art. For example, a compound of formula I wherein —F—G— represents —C=CH— initially obtained may be readily converted into the corresponding compound wherein —F—G— represents —CH—CH$_2$— by conventional catalytic hydrogenation procedures. A compound of formula I initially obtained wherein Q is substituted by hydroxy may be converted into the corresponding compound wherein Q is substituted by an oxo moiety by treatment with an oxidizing agent, suitably sulphur trioxide-pyridine complex. In addition, a compound of formula I wherein $R^1$ is benzyl initially obtained may be converted by catalytic hydrogenation to the corresponding compound of formula III, which in turn may be converted into a further compound of formula I using standard N-alkylation techniques as described above. Furthermore, a compound of formula I initially obtained wherein the $R^1$ moiety is substituted by nitro or cyano may be converted by catalytic hydrogenation to the corresponding amino- or aminomethyl-substituted compound respectively. Additionally, a compound of formula I wherein the $R^1$ moiety is substituted by hydroxymethyl may be obtained by lithium aluminium hydride reduction of a precursor alkoxycarbonyl derivative; the resulting hydroxy compound may then be be mesylated under standard conditions, and the mesyl group subsequently displaced by an amino moiety by treatment with the desired amine in a sealed tube at an elevated temperature. The amine derivative resulting from any of these procedures may then, for example, be N-acylated using the appropriate acyl halide, e.g. acetyl chloride; or aminocarbonylated, using potassium isocyanate, to the corresponding urea derivative; or converted to a 1,2,4-triazol-4-yl derivative using N,N-dimethylformamide azine; or reductively alkylated by treatment with the appropriate aldehyde or ketone in the presence of sodium cyanoborohydride. If desired, the amine derivative may also be carbamoylated by treatment with the requisite alkyl chloroformate. A compound of formula I initially obtained wherein the $R^1$ moiety is substituted by cyano may be converted, by treatment with sodium azide, to the corresponding tetrazole derivative, which in turn may be alkylated on the tetrazole ring by treatment with an alkyl halide under standard conditions. By way of additional illustration, a compound of formula I initially obtained wherein the $R^1$ moiety is substituted by an alkoxycarbonyl moiety may be saponified, by treatment with an alkali metal hydroxide, to the corresponding carboxy-substituted compound, which in turn may be converted to an amide derivative by treatment with the appropriate amine, advantageously in the presence of 1-(3-dimethylaminopropyl)-3-ethylcarbodiimide hydrochloride and 1-hydroxybenzotriazole. Alternatively, a compound of formula I initially obtained wherein the $R^1$ moiety is substituted by an alkoxycarbonyl moiety may be converted directly to an amide derivative by treatment with the appropriate amine in a sealed tube at an elevated temperature, or in the presence of trimethylaluminium. Moreover, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-HT$_{1D_\alpha}$ receptor subtype, inhibit forskolin-stimulated adenylyl cyclase activity, and stimulate [$^{35}$S]-GTPγS binding to membranes from clonal cell lines expressing human cloned receptors.

5-HT$_{1D_\alpha}$/5-HT$_{1D_\beta}$ Radioligand Binding

Chinese hamster ovary (CHO) clonal cell lines expressing the human 5-HT$_{1D_\alpha}$ and 5-HT$_{1D}\beta$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, CaCl$_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 µM) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which IC$_{50}$ (the molar concentration of compound necessary to inhibit binding by 50%) values could be calculated for each test compound. The IC$_{50}$ values for binding to the 5-HT$_{1D_\alpha}$ receptor subtype obtained for the compounds of the accompanying Examples were below 100 nM in each case. Furthermore, the compounds of the accompanying Examples were all found to possess a selective affinity for the 5-HT$_{1D_\alpha}$ receptor subtype of at least 10-fold relative to the 5-HT$_{1D_\beta}$ subtype.

5-HT$_{1D_\alpha}$/5-HT$_{1D_\beta}$ Adenylyl Cyclase Assay

Studies were performed essentially as described in *J. Pharmacol. Exp. Ther.*, 1986, 238, 248. CHO clonal cell lines expressing the human cloned 5-HT$_{1D_\alpha}$ and 5-HT$_{1D_\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was incubated, for 10–15 min, in a final volume of 50 μl, at 30° C., with or without forskolin (10 μM), in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM MgCl$_2$, 1 mM EGTA, 1 mM 3-isobutyl-1-methylxanthine, 3.5 mM creatinine phosphate, 0.2 mg/ml creatine phosphokinase, 0.5–1 μCi α-[$^{33}$P]-ATP and 1 nCi [$^3$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which E$_{max}$ (maximal effect) and EC$_{50}$ (the molar concentration of compound necessary to inhibit the maximal effect by 50%) values were obtained for each test compound. Of those compounds which were tested in this assay, the EC$_{50}$ values for the 5-HT$_{1D_\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D_\alpha}$ receptor subtype relative to the 5-HT$_{1D_\beta}$ subtype.

5-HT$_{1D_\alpha}$/5-HT$_{1D_\beta}$ GTPγS Binding

Studies were performed essentially as described in *Br. J. Pharmacol.*, 1993, 109, 1120. CHO clonal cell lines expressing the human cloned 5-HT$_{1D_\alpha}$ and 5-HT$_{1D_\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, MgCl$_2$ 10, pargyline 0.01; ascorbate 0.1%; pH 7.4 at room temperature) at a concentration of 40 μg protein/ml for the 5-HT$_{1D_\alpha}$ receptor transfected cells and 40–50 μg protein/ml for the 5-HT$_{1D_\beta}$ receptor transfected cells. The membrane suspension was then incubated, in a volume of 1 ml, with GDP (100 μM for 5-HT$_{1D_\alpha}$ receptor transfected cells, 30 μM for the 5-HT$_{1D_\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which E$_{max}$ (maximal effect) and EC$_{50}$ (the molar concentration of compound necessary to inhibit the maximal effect by 50%) values were obtained for each test compound. Of those compounds which were tested in this assay, the EC$_{50}$ values for the 5-HT$_{1D_\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D_\alpha}$ receptor subtype relative to the 5-HT$_{1D_\beta}$ subtype.

DESCRIPTION 1

4-(1,2,4-Triazol-4-yl)phenylhydrazine

Prepared as described in WO 94/03446, Example 1.

DESCRIPTION 2

4-[3-(5-(1,2,4-Triazol-4-yl)-1H-indol-3-yl)propyl] piperidine a) 5-(4-Pyridyl)pent-4-yn-1-ol 4-Bromopyridine hydrochloride (5 g, 0.031 mol) was partitioned between 2N NaOH (50 ml) and ethyl acetate (250 ml). The organic layer was collected, dried over MgSO$_4$ and evaporated in vacuo. The resulting oil was dissolved in triethylamine (10 ml) and degassed with nitrogen. Pent-4-yn-1-ol (3 g, 0.035 mol) was added, followed by bis (triphenylphosphine)palladium (II) chloride (200 mg) and copper iodide (100 mg). The reaction was heated to reflux and stirred for 15 min. The reaction was partitioned between ethyl acetate (250 ml) and water (50 ml). The organic layer was collected, dried over MgSO$_4$ and evaporated. The residue was chromatographed on silica eluting with ethyl acetate to afford the title compound as a yellow solid (3.14 g). $^1$H NMR (250 MHz, CDCl$_3$) 1.8 (1H, br s), 1.87 (2H, q), 2.57 (2H, t), 3.81 (2H, br t), 7.24 (2H, dd), 8.78 (2H, dd).

b) 5-(4-Pyridyl)-1-pentanol 5-(4-Pyridyl)pent-4-yn-1-ol (3.41 g) prepared according to the procedure described above was dissolved in ethanol (30 ml) and hydrogenated over palladium hydroxide catalyst (0.300 g) at 45 psi for 3 h. The catalyst was filtered and the ethanol evaporated in vacuo to yield the title product as a colourless oil (3.2 g). $^1$H NMR (250 MHz, CDCl$_3$) δ 1.40–1.45 (2H, m), 1.47–1.80 (4H, m), 2.00 (1H br s), 2.62 (2H, t), 3.64 (2H, t), 7.10 (2H, d), 8.45 (2H, d).

c) 5-[-1-(N-Benzyl)-1,2,5,6-tetrahydropyridin-4-yl]-1-pentanol

The alcohol from above was dissolved in acetone (150 ml) and benzyl bromide added. The reaction was heated to reflux for 3 h, cooled, hexane (50 ml) added, and the solid filtered. The white solid was washed with hexane, air dried and re-dissolved in 100 ml of 80% MeOH/H$_2$O. The reaction mixture was cooled to 0° C. and sodium borohydride (1.4 g) added, portionwise, and stirred at 0° C. for 15 min and then at reflux for 16 h. The methanol was removed in vacuo, the residue partitioned between EtOAc (250 ml) and water (50 ml), and the organic layer collected. The ethyl acetate layer was dried (MgSO$_4$) and filtered, and removed in vacuo to yield 4.5 g of the title compound as a colourless oil (91% yield). $^1$H NMR (250 MHz, CDCl$_3$) δ 1.30–1.59 (6H, m), 1.97 (2H, br t), 2.06 (2H, m), 2.54 (2H, t), 2.95 (2H, m), 2.57 (2H, s), 3.63 (2H, t), 5.35 (1H, br m), 7.22 7.37 (5H, m).

d) 5-(N-tert-Butoxycarbonyl-4-piperidinyl)-1-pentanol

5-[1-(N-Benzyl)-1,2,5,6-tetrahydropyridin-4-yl]-1-pentanol (Description 2c) (48.7 g, 0.19 mol) was dissolved in methanol (300 ml) and purged with nitrogen. Palladium hydroxide on carbon (4 g) was added followed by ammonium formate (50 g) and the reaction stirred at reflux for 1 h. The reaction was filtered through Celite and concentrated in vacuo. The residue was redissolved in dichloromethane (250 ml) and treated with di-tert-butyldicarbonate (45.61 g). After 1 hour the reaction was concentrated in vacuo and purified on silica eluting with 50–80% EtOAc/hexane to yield 40.6 g (79%) of the title compound as a colourless oil. $^1$H NMR (250 MHz, CDCl$_3$) δ 1.45 (9H, s), 1.99 (1H, m), 1.26–1.3 (6H, m), 1.37–1.70 (6H, m), 2.66 (2H, dt), 3.64 (2H, t), 4.08 (2H, br d).

e) 5-(N-tert-Butoxycarbonyl-4-piperidinyl)-1pentanal

The alcohol (1.59 g, 0.0055 mol) from Description 2d was dissolved in anhydrous DMSO (20 ml) and triethylamine (3.8 ml, 0.027 mol) added. Sulfurtrioxide pyridine complex (1.32 g, 0.0083 mol) was added portionwise and the reaction stirred for 0.5 h. The reaction was diluted with EtOAc (70 ml) and poured into water (30 ml). The organic layer was collected and washed with water (3×30 ml), dried over MgSO$_4$, and the solvent removed in vacuo. The residue was used directly in Description 2e without further purification.

f) 4-[3-(5-(1,2,4-Triazol-4-yl)-1H-indol-3-yl)propyl] piperidine

A 4% H$_2$SO$_4$ solution (25 ml) was heated to 50° C. for 30 min while bubbling N$_2$ through the solution. 4-(1,2,4-Triazol-4-yl)phenylhydrazine (Description 1) (1.06 g, 0.0061 mol) was added to the acid solution followed by a solution of the aldehyde from Description 2e (1.5 g, 0.005 mol) in dichloromethane. The reaction was heated to reflux using an air-cooled condenser and a N$_2$ bubbler for 2 h. The reaction was cooled to 0° C. and aqueous NH$_3$ added till pH>8. The product was extracted into ethyl acetate (3×100 ml), dried over MgSO$_4$ and the solvent removed in vacuo. The residue was chromatographed on alumina eluting with CH$_2$Cl$_2$→1–5% MeOH/CH$_2$Cl$_2$ and finally 5:1:94 MeOH/NH$_3$/CH$_2$Cl$_2$. The title compound was obtained as a pale yellow foam (0.630 g). $^1$H NMR (250 MHz, CDCl$_3$) δ 1.1 (1H, m), 1.23–1.28 (3H, m), 1.68–1.79 (5H, m), 2.57 (2H, dt, J=1.5 Hz), 2.74 (2H, t, J=3 Hz), 3.05 (2H, br d, J=5 Hz), 7.14 (2H, m, indole-H), 7.47 (1H, d, J=2 Hz, indole-H), 7.54 (1H, d, indole-H), 8.46 (s, Ar-H (triazole)), 8.60 (br s, NH (indole)), MS: m/z 309 (M+1).

EXAMPLE 1

4-[3-(5-(1,2,4-Triazol-4-yl)-1H-indol-3-yl)propyl]-1-[2-(2-fluorophenyl)ethyl]piperidine. Bis Hydrochloride The product of Description 2 (0.2 g, 0.65 mmol), potassium carbonate (0.270 g, 1.95 mmol) and 2-fluorophenethyl bromide (0.131 g, 0.65 mmol) were dissolved in propan-2-ol (5 ml) and heated to reflux for 16 hours. The solvent was removed and the residue was dissolved in ethyl acetate/methanol and washed with saturated potassium carbonate soln. The organic extract was dried (MgSO$_4$), filtered and evaporated to yield the crude product which was purified on silica using 1–3% methanol/dichloromethane with 0.1% ammonium hydroxide. The resulting oil was treated with excess methanolic hydrochloric acid to yield the title product (0.09 g). $^1$H NMR (360 MHz, d$_4$ MeOH) δ 9.82 (2H, s), 7.70 (1H, s), 7.58 (1H, d, J=8.5 Hz), 7.25–7.17 (4H, m), 7.09–6.98 (2H, m), 2.99 (2H, bd, J=10.8 Hz), 2.86–2.74 (4H, m), 2.56–2.51 (2H, m), 2.08–2.02 (2H, m), 1.74–1.71 (4H, m), 1.35–1.22 (5H, m), MS (ES$^+$) 432 (M+H)$^+$. Found: C, 57.35; H, 6.80; N, 12.41. C$_{26}$H$_{29}$FN$_5$. 2HCl. 2.35H$_2$O requires C, 57.10; H, 6.77; N, 12.81%.

EXAMPLE 2

4-[3-(5-(1,2,4-Triazol-4-yl)-1H-indol-3-yl)propyl]-1-[2-(3-fluorophenyl)ethyl)]piperidine Prepared according to the method of Example 1 using 2-(3-fluorophenyl)ethyl bromide.

$^1$H NMR (360 MHz, d$_4$ MeOH) δ 8.46 (2H, s), 8.35 (1H, s), 7.54 (1H, d, J=2 Hz), 7.47 (1H, d, J=8.5 Hz), 7.26–7.13 (3H, m), 6.98–6.86 (3H, m), 3.15–2.90 (2H, m), 2.85–2.79 (2H, m), 2.75 (2H, t, J=7.6 Hz), 2.54–2.68 (2H, m), 1.97–2.12 (2H, m), 1.82–1.65 (4H, m), 1.24–1.45 (5H, m), MS (ES$^+$) 432 (M+H)$^+$. Found: C, 72.04; H, 7.11; N, 15.48. C$_{26}$H$_{30}$FN$_5$ requires C, 73.36; H, 7.00; N, 16.23%.

EXAMPLE 3

4-[3-(5-(1,2,4-Triazol-4-yl)-1H-indol-3-yl)propyl]-1-[2-(4-(trifluoromethyl)phenyl)ethyl]piperidine Prepared according to the method of Example 1 using 2-[4-(trifluoromethyl)phenyl]ethyl bromide.

NMR (250 MHz, CDCl$_3$) δ 8.47 (2H, s), 8.31 (1H, s), 7.55–7.46 (4H, m), 7.33–7.26 (1H, s), 7.17–7.14 (2H, m), 3.20–2.88 (4H, m), 2.88–2.60 (4H, m), 2.20–2.00 (2H, m), 1.85–1.18 (9H, m), MS (ES$^+$) 482 (M+H)$^+$. Found: C, 66.91; H, 6.20; N, 14.06. C$_{27}$H$_{30}$F$_3$N$_5$. (0.25)H$_2$O requires C, 66.72; H, 6.32; N, 14.41%.

EXAMPLE 4

4-[3-(5-(1,2,4-Triazol-4-yl)-1H-indol-3-yl)propyl]-1-[3-(phenyl)propyl]piperidine The product of Description 2 (0.2 g, 0.65 mmol) and hydrocinnamaldehyde (0.09 ml, 0.66 mmol) were stirred together in methanol (5 ml). Acetic acid (1 ml) and sodium cyanoborohydride (0.041 g, 0.66 mmol) were added and the reaction was stirred for 16 hours. The solvent was removed and the residue was partitioned between ethyl acetate/butanol and potassium carbonate solution. The organic layer was concentrated and the residue was purified by column chromatography on silica using 1–3% methanol/dichloromethane with 0.1% ammonium hydroxide to yield the title compound as a white solid (0.089 g). $^1$H NMR (250 MHz, CDCl$_3$) δ 8.48 (1H, s), 8.46 (2H, s), 7.53 (1H, d, J=2 Hz), 7.47 (1H, d, J=8.5 Hz), 7.30–7.12 (6H, m), 3.04–2.92 (2H, m), 2.98–2.68 (2H, m), 2.68–2.58 (2H, m), 2.45–2.34 (2H, m), 2.02–1.68 (4H, m), 1.42–1.20 (5H, m), MS (ES$^+$) 428 (M+H)$^+$. Found: C, 76.17; H, 7.85; N, 15.52. C$_{27}$H$_{33}$N$_5$ requires C, 75.84; H, 7.78; N, 15.52%.

EXAMPLE 5

(±)-4-[3-(5-(1,2,4-Triazol-4-yl)-1H-indol-3-yl)-propyl]-1-[2-(phenyl)-propyl]piperidine. Bis Oxalate Prepared according to the method of Example 4 using the compound from Description 2 and 2-phenylpropionaldehyde.

$^1$H NMR (250 MHz, d$_6$-DMSO) δ 11.18 (1H, s), 9.15 (2H, s), 7.89 (1H, d, J=2 Hz), 7.59 (1H, d, J=8.3 Hz), 7.44–7.28 (6H, m), 3.04–2.77 (4H, m), 2.46–2.43 (2H, m), 2.01–1.70 (6H, m), 1.48–1.12 (5H, m), 1.28 (3H, d, J=6.8 Hz), MS (ES$^+$) 428 (M+H)$^+$. Found: C, 58.40; H, 6.35; N, 10.60. C$_{27}$H$_{33}$N$_5$. 2(CO$_2$H)$_2$. 1.75(H$_2$O) requires C, 58.25; H, 6.39; N, 10.95%.

EXAMPLE 6

4-[3-(5-(1,2,4-Triazol-4-yl)-1H-indol-3-yl)propyl]-1-[2-(3,4-difluorophenyl)ethyl]piperidine Prepared according to the method of Example 4 using the compound from Description 2 and 3,4-difluorophenylacetaldehyde.

NMR (360 MHz, d$_6$ DMSO) δ 11.18 (1H, s), 9.55 (2H, s), 7.88 (1H, d, J=2 Hz), 7.54–7.13 (6H, m), 3.55–3.43 (2H, m), 3.28–3.07 (2H, m), 3.07–2.84 (4H, m), 2.78–2.68 (2H, m), 1.96–1.82 (2H, m), 1.76–1.24 (7H, m), MS (ES$^+$) 450 (M+1)$^+$.

EXAMPLE 7

4-[3-(5-(1,2,4-Triazol-4-yl)-1H-indol-3-yl)propyl]-1-benzylpiperidine

Prepared according to the method described for Example 4 using the compound from Description 2 and benzaldehyde. MS (ES) 400 (M+1). $^1$H NMR (250 MHz, CDCl$_3$) δ 1.25–1.36 (4H, m), 1.68 (5H, m), 1.92 (2H, br t), 2.73 (2H, t, J=3 Hz), 2.87 (2H, d, J=5 Hz), 3.47 (2H, s), 7.13 (2H, m), 7.26 (5H, m), 7.46 (1H, d, J=4 Hz), 7.53 (1H, d), 8.37 (br s, NH (indole)), 8.46 (2H, s, Ar(H) triazole). Oxalate salt: C$_{25}$H$_{29}$N$_5$. 1.6(COOH)$_2$ calculated for: C, 62.30; H, 5.97; N, 12.88%; found C, 62.23; H, 6.07; N, 12.82%.

EXAMPLE 8

4-[3-(5-(1,2,4-Triazol-4-yl)-1H-indol-3-yl)propyl]-1-(2-tert-butylethyl)-piperidine Prepared according to the method described for Example 4 using the compound from Description 2 and 3,3-dimethylbutyraldehyde. MS (ES) 394 (M+1). $^1$H NMR (250 MHz, CDCl$_3$) δ 0.88 (9H, s), 1.13–1.43 (7H, m), 1.66–1.91 (6H, m), 2.26–2.33 (2H, m), 2.74 (2H, t, J=3 Hz), 2.93 (2H, bd, J=4 Hz), 7.13 (2H, m), 7.47 (1H, d, J=2 Hz), 7.54 (1H, d, J=1 Hz), 8.47 (2H, s, Ar(H) triazole), 8.64 (br s, NH (indole)). Oxalate salt C$_{24}$H$_{35}$N$_5$. C$_2$H$_2$O$_4$ calculated for C, 58.53; H, 7.25; N, 12.50; found C, 58.78; H, 7.05; N, 12.51%.

EXAMPLE 9

4-[3-(5-(1,2,4-Triazol-4-yl)-1H-indol-3-yl)prolyl]-4-(2-phenylethyl)-piperidine Prepared according to the method described for Example 4 using the compound from Description 2 and phenylacetaldehyde. MS (ES) 414 (M+1). $^1$H NMR (250 MHz, CDCl$_3$) δ 1.28–1.39 (5H, m), 1.72 (4H, m), 198 (2H, br t), 2.53–2.59 (2H, m), 2.72–2.84 (4H, m), 3.0 (2H, br d, J=3 Hz), 7.12–7.30 (7H, m), 7.47 (1H, d, J=3 Hz), 7.54 (1H, d, J=3 Hz), 7.54 (1H, d, J=1 Hz), 8.47 (2H, s, ArH (triazole)), 8.48 (br s, indole (NH)). Oxalate salt C$_{26}$H$_{31}$N$_5$. C$_2$H$_2$O$_4$ calculated for C, 60.81; H, 6.13; N, 11.98; found C, 60.77; H, 6.05; N, 12.38%.

DESCRIPTION 3

4-[3-(5-(1,2,4-Triazol-4-yl)-1H-indol-3-yl)propyl]-1-(α-methoxycarbonylbenzyl)piperidine 4-[3-(5-(1,2,4-Triazol-4-yl)-1H-indol-3-yl)propyl] piperidine (Description 2, 0.800 g, 0.0026 mol) was dissolved in anhydrous DMF (10 ml), under N$_2$, and potassium carbonate (0.540 g, 0.0039 mol) added followed by (±)-methyl α-bromophenylacetate (Aldrich, 0.5 ml, 0.0031 mol). The reaction was stirred at 25° C. for 16 h, then poured into ethyl acetate (100 ml) and H$_2$O (30 ml). The organic layer was collected, washed with H$_2$O (3×30 ml), dried over MgSO$_4$ and evaporated with 1–5% MeOH/CH$_2$Cl$_2$ to obtain the title compound as a colourless oil. $^1$H NMR 1.23–1.33 (6H, m), 1.66 (5H, m), 2.04 (1H, br m), 2.72 (2H, t, J=3 Hz), 2.96 (1H, bm), 3.69 (3H, s), 3.98 (1H, br s), 7.11 (1H, d, J=1 Hz), 7.14 (1H, d, J=2 Hz), 7.33 (3H, m), 7.43–7.48 (2H, m), 7.50 (1H, d, J=3 Hz), 7.51 (1H, d, J=1 Hz), 8.07 (br s, indole (NH)), 8.45 (2H, s, Ar (triazole)).

EXAMPLE 10

N-Methyl-2-phenyl-2-[4-(3-(5-(1,2,4-triazol-4-yl)-1H-indol-3-yl)propyl)piperidin-1-yl]acetamide The compound from Description 3 (0.530 g) was dissolved in a solution of methylamine in methanol (≈5M, 10 ml) and heated at 70° C. in a sealed tube for 24 h. The tube was cooled, and the contents evaporated. The residue was chromatographed on silica gel eluting with 1–5% MeOH/CH$_2$Cl$_2$ to obtain the title compound as a colourless oil (0.220 g). MS (ES) 456 (M+1). $^1$H NMR (250 MHz, CDCl$_3$) δ 1.23–1.28 (6H, m), 1.69 (5H, m), 2.06 (1H, br m), 2.72 (2H, t, J=3 Hz), 2.85 (3H, d, J=2 Hz), 2.96 (1H, br m), 3.85 (1H, br s), 7.11 (1H, dt, J=1 Hz), 7.13 (1H, J=1 Hz), 7.27 (5H, m), 7.46 (1H, d, J=3 Hz), 7.51 (1H, d, J=1 Hz), 8.46 (3H, s, ArH (triazole)$^+$indole (NH)).

EXAMPLE 11

4-[3-(5-(1,2,4-Triazol-4-yl)-1H-indol-3-yl)propyl]-1-(1-(phenyl-2-hydroxyethyl)piperidine The compound from Description 3 (0.800 g, 0.00175 mol) was dissolved in anhydrous THF (10 ml) and lithium aluminium hydride (0.5M in DME, 2.3 ml, 0.0023 mol) added dropwise at 0° C. The reaction was stirred at 0° C. for 20 min, and quenched by the slow addition of cold saturated NH$_4$Cl solution. The reaction was poured into EtOAc (50 ml)/NH$_4$Cl (20 ml), the organic layer collected, dried over MgSO$_4$ and evaporated. The residue was purified on silica eluting with 5% MeOH/1% NH$_3$/94% CH$_2$Cl$_2$ to obtain the title compound as a colourless oil (0.720 g). MS (ES) 430 (M+1). $^1$H NMR (250 MHz, CDCl$_3$) δ 1.18–1.28 (4H, m), 1.43 (4H, m), 2.05 (2H, br t), 2.70 (2H, t, J=3 Hz), 2.87 (2H, br d), 3.54–3.75 (2H, m), 4.00 (1H, t, J=4 Hz), 7.12–7.19 (4H, m), 7.26 (3H, m), 7.46 (1H, d, J=3 Hz), 7.50 (1H, d, J=1 Hz), 8.39 (br s, indole-NH), 8.47 (2H, s, ArH (triazole)) oxalate salt.

EXAMPLE 12

4-[3-(5-(1,2,4-Triazol-4-yl)-1H-indol-3-yl)propyl]-1-[2-(2-chlorophenyl)propyl]pineridine Step 1: 2-(2-Chlorophenyl)-1-methoxypropene To a stirred solution of methoxymethyl triphenylphosphonium chloride (16.6 g, 0.0484 mol) in THF (120 ml) at −78° C., was added n-butyl lithium (26 ml of a 1.6 M solution in hexanes, 0.042 mol) dropwise. The mixture was stirred at −78° C. for 30 min then at −20° C. for 30 min. The solution was cooled to −78° C. and a solution of 2-chloroacetophenone (5.0 g, 0.032 mol) in THF (10 ml) was added dropwise. After addition the mixture was allowed to warm to room temperature then stirred overnight. The undissolved solid was removed by filtration and the filtrate washed with water (100 ml). The organic layer was separated, dried (Na2SO$_4$) and evaporated. The residue was chromatographed on silica, using petrol:ether (25:1) as the eluant, to give the (E)- and (Z)-enol ethers (1.5 g, 26%) as a colourless oil. $^1$H NMR (250 MHz, CDCl$_3$) δ 1.87 and 1.95 (3H, 2×d, J=1.5 and 1.4 Hz respectively), 3.52 and 3.70 (3H, 2×s), 6.04 (1H, m), 7.14–7.40 (4H, m).

Step 2: 2-(2-Chlorophenyl)propanal

To a solution of 2-(2-chlorophenyl)-1-methoxypropene (712 mg, 3.9 mmol) in ether (8 ml) at 0° C. was added perchloric acid (70%, 3 ml). After stirring for 1 h the solution was diluted with ether (8 ml) and washed with water (2×20 ml). The organic phase was separated, dried ($Na_2SO_4$) and evaporated. The crude 2-(2-chlorophenyl)propanal was isolated as a colourless oil and used without further purification.

Step 3: 4-[3-(5-(1,2,4-Triazol-4-yl)-1H-indol-3-yl)propl]-1-[2-(2-chlorophenyl)propyl]piperidine Prepared according to the method of Example 4, using the compound from Description 2 and 2-(2-chlorophenyl) propanal. $^1$H NMR (360 MHz, $CDCl_3$) δ 1.20–1.40 (8H, m), 1.55–1.77 (4H, m), 1.90–2.10 (2H, m), 2.38–2.60 (2H, m), 2.73 (2H, t, J=7.5 Hz), 2.80–2.92 (1H, m), 2.96–3.10 (1, m), 3.46–3.60 (1H, m), 7.07–7.13 (3H, m), 7.15–7.27 (2H, m), 7.32 (1H, d, J=7.9 Hz), 7.46 (1H, d, J=8.5 Hz), 7.53 (1H, s), 8.31 (1H, br s), 8.46 (2H, s). MS ($ES^+$) 462/464 $(M+1)^+$. Found: C, 67.58; H, 6.61; N, 14.56%. $C_{27}H_{32}N_5Cl0.9$ ($H_2O$) requires: C, 67.81; H, 7.12; N, 14.64%.

EXAMPLE 13

4-[3-(5-(1,2,4-Triazol-4-yl)-1H-indol-3-yl)proyl]-1-[2-(2-trifluoromethylphenyl)propyl]-piperidine Oxalate Step 1: 1-Methoxy-2-(2-trifluoromethylphenyl)propene Prepared according to the method of Example 12, Step 1 using 2-trifluoromethylacetophenone. $^1$H NMR (250 MHz, $CDCl_3$) δ 1.86 and 1.92 (3H, 2×d, J=1.5 and 1.4 Hz respectively), 3.49 and 3.66 (3H, 2×s), 5.90 and 5.98–6.00 (1H, br s and m respectively), 7.02–7.38 (2H, m), 7.44–7.54 (1H, m), 7.62–7.68 (1H, m).

Step 2: 2-(2-Trifluoromethylphenyl)propanal

Prepared according to the method of Example 12, Step 2, using 1-methoxy-2-(2-trifluoromethylphenyl)propene. The crude product was used directly without further purification. $^1$H NMR (250 MHz, $CDCl_3$) δ 1.45 (3H, d, J=7.0Hz), 4.09 (1H, q, J=7.0Hz), 7.22 (1H, d, J=7.8 Hz), 7.41 (1H, J=7.7 Hz), 7.57 (1H, t, J=7.6 Hz), 7.73 (1H, d, J=7.5 Hz), 8.71 (1H, s).

Step 3: 4-[3-(5-(1,2,4-Triazol-4-yl)-1H-indol-3-yl)propyl]-1-[2-(2-trifluoromethylphenyl)propyl]piperidine Oxalate Prepared according to the method of Example 4, using the compound from Description 2 and 2-(2-trifluoromethylphenyl)propanal. $^1$H NMR (360 MHz, $d_6$-DMSO) δ 1.24–1.50 (8H, m), 1.60–1.81 (4H, m), 2.69 (2H, t, J=7.5 Hz), 3.04–3.30 (2H, m), 3.38–3.51 (1H, m), 3.60–3.80 (4H, m), 7.26–7.32 (2H, m), 7.46–7.50 (2H, m), 7.68–7.72 (3H, m), 7.76 (1H, s), 9.01 (2H, s), 11.07 (1H, br s). MS ($ES^+$) 496 $(M+1)^+$. Found: C, 59.51; H, 5.90; N, 11.11%. $C_{28}H_{32}N_5F_3$. 1.4($C_2H_2O_4$) requires: C, 59.51; H, 5.64; N, 11.27%.

EXAMPLE 14

4-[3-(5-(1,2,4-Triazol-4-yl)-1H-indol-3-yl)propyl]-1-[2-(4-chlorophenyl)propyl]piperidine. Oxalate Step 1: 1-Methoxy-2-(4-chlorophenyl)propene Prepared according to the method of Example 12, Step 1, using 4-chloroacetophenone. $^1$H NMR (360 MHz, $CDCl_3$) δ 1.89 and 1.95 (3H, 2×d, J=1.3 Hz each), 3.67 and 3.71 (3H, 2×s), 6.10–6.14 and 6.38–6.40 (1H, 2×m), 7.17–7.29 (3H, m), 7.53–7.56 (1H, m).

Step 2: 2-(4-Chlorophenyl)propanal

Prepared according to the method of Example 12, Step 2, using 1-methoxy-2-(4-chlorophenyl)propene. The crude aldehyde was used directly without further purification.

Step 3: 4-[3-(5-(1,2,4-Triazol-4-yl)-1H-indol-3-yl)propyl]-1-[2-(4-chlorophenyl)propyl]piperidine. Oxalate Prepared according to the method of Example 4, using the compound from Description 2 and 2-(4-chlorophenyl) propanal. $^1$H NMR (360 MHz, $d_6$-DMSO) δ 1.20–1.56 (8H, m), 1.61–1.84 (4H, m), 2.61–2.88 (4H, m), 3.16–3.36 (5H, m), 7.25–7.32 (2H, m), 7.36–7.42 (4H, m), 7.47 (1H, d, J=8.6 Hz), 7.76 (1H, s), 9.01 (2H, s), 11.09 (1H, br s). MS ($ES^+$) 462 $(M+1)^+$. Found: C, 60.14; H, 6.44; N, 11.80%. $C_{27}H_{32}N_5Cl$. 1.3($C_2H_2O_4$). 0.5 ($H_2$) requires: C, 60.45; H, 6.10; N, 11.91%.

EXAMPLE 15

4-[3-(5-(1,2,4-triazol-4-yl)-1H-indol-3-yl)propyl]-1-[2-methoxyphenyl)phenyl]-piperidine. Oxalate Step 1: 1-Methoxy-2-(4-methoxyphenyl)propene Prepared according to the method of Example 12, Step 1 using 4-methoxyacetophenone. $^1$H NMR (250 MHz, $CDCl_3$) δ 1.90 and 2.00 (3H, 2×d, J=1.3 Hz each), 3.66 and 3.70 (3H, 2×s), 3.80 and 3.81 (3H, 2×s), 6.04–6.07 and 6.30–6.34 (1H, 2×m), 6.83–6.90 (2H, m), 7.19–7.28 (1H, m), 7.51–7.59 (1H, m).

Step 2: 2-(4-Methoxyphenyl)propanal

Prepared according to the method of Example 12, Step 2 using 1-methoxy-2-(4-methoxyphenyl)propene. The crude aldehyde was used directly without further purification.

Step 3: 4-[3-(5-(1,2,4-Triazol-4-yl)-1H-indol-3-yl)propyl]-1-[2-(4-methoxyphenyl)propyl]piperidine. Oxalate Prepared according to the method of Example 4, using the compound from Description 2 and 2-(4-methoxyphenyl) propanal. $^1$H NMR (360 MHz, $d_6$-DMSO) δ 1.17–1.59 (7H, m), 1.60–1.76 (5H, m), 2.42–2.90 (5H, m), 3.12–3.44 (4H, m), 3.74 (3H, s), 6.91 (2H, d, J=8 Hz), 7.20–7.34 (4H, m 7.48 (1H, d, J=8.2 Hz), 7.77 (1H, s), 9.01 (2H, s), 11.09 (1H, br s). MS ($ES^+$) 458 $(M+1)^+$. Found: C, 61.08; H, 6.56; N, 10.78%. $C_{28}H_{35}N_5O$. 1.9($C_2H_2O_4$) requires: C, 60.75; H, 6.22; N, 11.14%.

EXAMPLE 16

4-[3-(5-(1,2,4-Triazol-4-yl)-1H-indol-3-yl)propyl]-1-[2-(2,6-dichlorophenyl)propyl]piperidine Step 1: Ethyl (2,6-dichlorophenyl)acetate To a solution of 2,6-dichlorophenyl acetic acid (6.7 g, 0.033 mol) in dichloromethane (170 ml) was added triethylamine (5.9 ml, 0.043 mol), 1-ethyl-3-(3-dimethylaminopropyl)carbodiimide hydrochloride (8.1 g, 0.043 mol) and 4-pyrrolidinopyridine (0.58 g, 0.004 mol). Ethanol (2.5 ml, 0.043 mol) was added dropwise and the solution stirred overnight at room temperature. After this time the mixture was washed with water (2×100 ml), 1M HCl (2×100 ml), aq. $K_2CO_3$ (sat.; 2×100 ml) and brine (100 ml). The organic phase was separated, dried ($Na_2SO_4$) and evaporated. The residue was chromatographed on silica, using petrol:ether (10:1) as the eluant, to give the ester (7.2 g, 94%) as a colourless oil which solidified on standing at 0° C. $^1$H NMR (360 MHz, $d_6$-DMSO) δ 1.26 (3H, t, J=7.1 Hz), 4.01 (2H, s), 4.18 (2H, q, J=7.1 Hz), 7.15 (1H, t, J=8.6 Hz), 7.32 (2H, d, J=8.6 Hz).

Step 2: Ethyl 2-(2,6-dichlorolphenyl)propanoate

To a solution of diisopropylamine (1.3 ml, 9.4 mmol) in THF (20 ml) at 0° C. was added n-butyl lithium (5.9 ml of a 1.6M solution in hexane, 9.4 mmol) dropwise. The solution was stirred at 0° C. for 30 min then cooled to −78° C. A solution of ethyl (2,6-dichlorophenyl)acetate (2.0 g, 8.6 mmol) in THF (20 ml) was added dropwise and the solution stirred at −78° C. for 1 h. Iodomethane (0.59 ml, 9.4 mmol) was then added and the solution stirred at −78° C. for 15 min before the cooling was removed. The solution was allowed to warm to room temperature then NH₄Cl (sat., 20 ml) was added. The organic phase was separated and washed with 1M HCl (2×20 ml) followed by water (20 ml). The organic layer was separated, dried (Na₂SO₄) and evaporated. The residue was chromatographed on silica, using petrol:ether (15:1) as the eluant, to give the ester (0.66 g, 31%) as a colourless oil. ¹H NMR (360 MHz, CDCl₃) δ 1.21 (3H, t, J=7.1 Hz), 1.53 (3H, d, J=7.1 Hz), 4.01–4.24 (2H, m), 4.46 (1H, q, J=7.1 Hz), 7.12 (1H, t, J=7.9 Hz), 7.29 (2H, d, J=8.1 Hz).

Step 3: 2-(2,6-Dichlorophenyl)propan-1-ol

To a solution of ethyl 2-(2,6-dichlorophenyl)propanoate (0.66 g, 2.7 mmol) in THF (30 ml) at 0° C. was added diisobutylaluminium hydride (6.6 ml of a 1.0M solution in THF, 6.6 mmol) dropwise. The cooling bath was removed and the mixture stirred at room temperature for 45 min. More diisobutylaluminium hydride (3 ml of a 1.0M solution in THF, 3.0 mmol) was added and the solution stirred for a further 45 min. After this time more diisobutylaluminium hydride (3 ml of a 1.0M solution in THF, 3.0 mmol) was added and the solution stirred for 1 h. NH₄Cl (sat., 10 ml) was added and the mixture stirred at room temperature for 1 h. The organic layer was decanted off and the gelatinous precipitate partitioned between ether (30 ml) and 1M HCl (30 ml). The organic layers were combined, dried (Na₂SO₄) and evaporated. The residue was chromatographed on silica, eluting with petrol:EtOAc (3:1), to afford the alcohol (546 mg, 100%) as a colourless oil. ¹H NMR (250 MHz, CDCl₃) δ 1.41 (3H, d, J=6.7 Hz), 3.94–4.01 (2H, m), 4.13–4.23 (1H, m), 7.08 (1H, t, J=7.9 Hz), 7.20–7.40 (2H, m).

Step 4: 2-(2,6-Dichlorophenyl)propanal

To a stirred solution of 2-(2,6-dichlorophenyl)propan-1-ol (278 mg, 1.4 mmol) in DMSO (6 ml) was added triethylamine (1.1 ml, 8.1 mmol) followed by pyridine-sulphur trioxide (322 mg, 2.0 mmol). After 1 h more pyridine-sulphur trioxide (161 mg, 1.0 mmol) was added and the mixture stirred for a further 1 h. The mixture was partitioned between EtOAc (3×20 ml) and water (20 ml). The combined organic layers were washed with brine (20 ml) then separated and dried (Na₂SO₄). The solvent was evaporated and the residue azeotroped with toluene (2×20 ml). The aldehyde was used directly without further purification. ¹H NMR (250 MHz, CDCl₃) δ 1.51 (3H, d, J=7.0 Hz), 4.17 (1H, q, J=7.0 Hz), 7.20 (1H, t, J=8.0 Hz), 7.33 (2H, d, J=8.5 Hz).

Step 5: 4-[3-(5-(1,2,4-Triazol-4-yl)-1H-indol-3-yl)propyl]-1-[2-(2,6-dichlorophenyl)propyl]piperidine Prepared according to the method of Example 4, using the compound from Description 2 and 2-(2,6-dichlorophenyl) propanal. ¹H NMR (360 MHz, CDCl₃) δ 1.02–1.28 (5H, m), 1.32 (3H, d, J=7.2 Hz), 1.48–1.70 (4H, m), 1.82–2.00 (2H, m), 2.65 (2H, t, J=7.5 Hz), 2.67–2.80 (1H, m), 2.81–2.90 (3H, m), 3.79–3.89 (1H, m), 6.95 (1H, t, J=8.0 Hz), 7.01–7.06 (2H, m), 7.13–7.22 (2H, m), 7.39 (1H, d, J=8.5 Hz), 7.45 (1H, d, J=1.9 Hz), 8.39 (3H, s). MS (ES⁺) 496/498 (M+1)⁺. Found: C, 64.60; H, 6.37; N, 13.84%. C₂₇H₃₁N₅Cl₂. 0.3(H₂O) requires: C, 64.62; H, 6.35; N, 13.95%.

EXAMPLE 17

4-[3-(5-(1,2,4-Triazol-4-yl)-1H-indol-3-yl)propyl]-1-[2-(3-methoxyphenyl)propyl]piperidine. Oxalate Step 1: 1-Methoxy-2-(3-methoxyphenyl)propene Prepared according to the method of Example 12, Step 1, using 3-methoxyacetophenone. ¹H NMR (360 MHz, CDCl₃) δ 1.91 and 1.97 (3H, 2×d, J=1.3 Hz), 3.67 and 3.71 (3H, 2×s), 3.81 (3H, s), 6.11–6.12 and 6.42–6.43 (1H, 2×m), 6.72–6.92 (2H, m), 7.16–7.27 (2H, m).

Step 2: 2-(3-Methoxyphenyl)propanal

Prepared according to the method of Example 12, Step 12 using 1-methoxy-2-(3-methoxyphenyl)propene. The crude aldehyde was used directly without further purification.

Step 3: 4-[3-(5-(1,2,4-Triazol-4-yl)-1H-indol-3-yl)propyl]-1-[2-(3-methoxyphenyl)propyl]piperidine. Oxalate Prepared according to the method of Example 4, using the compound from Description 2 and 2-(3-methoxyphenyl) propanal. ¹H NMR (360 MHz, d₆-DMSO) δ 1.07–1.50 (8H, m), 1.60–1.80 (4H, m), 2.60–2.76 (4H, m), 3.04–3.34 (5H, m), 3.75 (3H, s), 6.80–6.84 (1H, m), 6.86–6.90 (2H, m), 7.22–7.30 (3H, m), 7.47 (1H, d, J=8.6 Hz), 7.75 (1H, d, J=1.9 Hz), 9.00 (2H, s), 11.09 (1H, br s). MS (ES⁺) 458 (M+1)⁺. Found: C, 64.91; H, 6.98; N, 12.55%. C₂₈H₃₅N₅O. (CO₂H)₂. 0.5(H₂O) requires: C, 64.73; H, 6.88; N, 12.58%.

EXAMPLE 18

4-[3-(5-(1,2,4-Triazol-4-yl)-1H-indol-3-yl)proyl]-1-[2-(2-methoxyphenyl)propyl]piperidine. Oxalate Step 1: 1-Methoxy-2-(2-methoxyphenyl)propene Prepared according to the method of Example 12, Step 1 using 2-methoxyacetophenone. ¹H NMR (360 MHz, CDCl₃) δ 1.87 and 1.96 (3H, 2×d, J=1.4 Hz), 3.54 and 3.68 (3H, 2×s), 3.82 and 3.83 (2H, 2×s), 6.02–6.05 and 6.20–6.22 (1H, 2×m), 6.85–6.96 (2H, m), 7.11–7.26 (2H, m).

Step) 2: 2-(2-Methoxyphenyl)propanal

Prepared according the method of Example 12, Step 2 using 1-methoxy-2-(2-methoxyphenyl)propene. The crude aldehyde was used directly without further purification. ¹H NMR (360 MHz, CDCl₃) δ 1.39 (3H, d, J=7.1 Hz), 3.83 (3H, s), 3.86 (1H, q, J=7.0 Hz), 6.92 (1H, d, J=8.0 Hz), 6.97 (1H, t, J=7.5 Hz), 7.11 (1H, dd, J=7.5 and 1.6 Hz), 7.26–7.31 (1H, m), 9.67 (1H, s).

Step 3: 4-[3-(5-(1,2,4-Triazol-4-yl)-1H-indol-3-yl)propyl]-1-[2-(2-methoxyphenyl)propyl]piperidine. Oxalate Prepared according to the method of Example 4, using the compound from Description 2 and 2-(2-methoxyphenyl) propanal. ¹H NMR (360 MHz, d₆-DMSO) δ 1.12–1.54 (8H, m), 1.64–1.84 (4H, m), 2.62–2.90 (4H, m), 3.08–3.20 (2H, m), 3.28–3.42 (2H, m), 3.48–3.56 (1H, m), 3.81 (3H, s), 6.95 (1H, t, J=7.3 Hz), 6.99 (1H, d, J=8.1 Hz), 7.23–7.32 (4H, m), 7.48 (1H, d, J=8.6 Hz), 7.77 (1H, d, J=1.9 Hz), 9.02 (2H, s), 11.10 (1H, br s). MS (ES⁺) 458 (M+1)⁺. Found: C, 63.95; H, 6.99; N, 12.26%. C₂₈H₃₆N₅O. (CO₂H)₂. H₂O requires: C, 63.70; H, 6.95; N, 12.38%.

EXAMPLE 19

4-[3-(5-(1,2,4-Triazol-4-yl)-1H-indol-3-yl)propyl]-1-[2-(3-chlorophenyl)propyl]piperidine. Oxalate.

Step 1: 2-(3-Chlorophenyl)-1-methoxypronene

Prepared according to the method of Example 12, Step 1, using 3-chloroacetophenone. ¹H NMR (360 MHz, CDCl₃) δ 1.89 and 1.96 (3H, 2×d, J=1.3 Hz), 3.69 and 3.73 (3H, 2×s), 6.14 and 6.43 (1H, 2×d, J=1.2 and 1.3 Hz respectively), 7.10–7.62 (4H, m).

Step 2: 2-(3-Chlorophenyl)propanal

Prepared according to the method of Example 12, Step 2, using 2-(3-chlorophenyl)-1-methoxypropene. The crude product was used directly without further purification.

Step 3: 4-[3-(5-(1,2,4-Triazol-4-yl)-1H-indol-3-yl)propyl]-1-[2-(3-chlorophenyl)propyl]piperidine. Oxalate Prepared according to the method of Example 4, using the compound from Description 2 and 2-(3-chlorophenyl) propanal. ¹H NMR (360 MHz, d₆-DMSO) δ 1.22–1.72 (8H, m), 1.60–1.80 (4H, m), 2.60–2.80 (4H, m), 3.08–3.34 (5H, m), 7.25–7.49 (7H, m), 7.76 (1H, d, J=2.0 Hz), 9.00 (2H, s), 11.08 (1H, br s). MS (ES⁺) 462 (M+1)⁺. Found C, 61.62: H, 6.49; N, 11.77%. $C_{27}H_{32}N_5Cl$. $1.25(CO_2H)_2$. $0.25(H_2O)$ requires: C, 61.19; H, 6.09; N, 12.09%.

EXAMPLE 20

4-[3-(5-(1,2,4-Triazol-4-yl)-1H-indol-3-yl)propyl]-1-[2-(3-aminosulphonylphenyl)propyl]piperidine. Oxalate Step 1: 3-Aminosulphonylacetophenone To a stirred solution of 3-acetylbenzene sulphonyl fluoride (0.5 g, 2.5 mmol) in THF (1 ml) at ambient temperature was added a solution of ammonia in water (25%, 1.35 ml), and the mixture stirred for 2 hours. The mixture was diluted with ethyl acetate (25 ml) and water (25 ml). The two layers were separated and the aqueous extracted with ethyl acetate (25 ml). The combined organic phases were dried ($MgSO_4$) and evaporated. The residue was chromatographed on silica using hexane:ethyl acetate (1:1), followed by ethyl acetate as the eluant, to give the title compound (0.31 g, 63%) as a colourless solid. ¹H NMR (360 MHz, $d_6$-DMSO) δ 2.65 (3H, s), 7.50 (2H, br s), 7.75 (1H, t, J=7.5 Hz), 8.06–8.08 (1H, m), 8.18–8.20 (1H, m), 8.35–8.36 (1H, m).

Step 2: 2-(3-Aminosulphonylphenyl)-1-methoxypropene

To a stirred solution of methoxymethyl triphenylphosphonium chloride (25.8 g, 75.4 mmol) in THF (150 ml) under nitrogen at −78° C. was added n-butyl lithium (37.7 ml of a 1.6M solution in hexanes, 60.3 mmol) dropwise. The mixture was stirred at −78° C. for 10 min and then at 0° C. for 45 min. The solution was cooled to −78° C. and a solution of 3-aminosulphonylacetophenone (5 g, 25.1 mmol) in THF (50 ml) was added dropwise. After addition the mixture was stirred at −78° C. for 1 h and then the mixture was allowed to warm to ambient temperature, then stirred for 16 h. $NH_4Cl$ solution (sat., 100 ml) was added to the mixture and the two phases separated. The aqueous phase was extracted with ether (100 ml) and the combined organic phases were dried ($Na_2SO_4$) and evaporated. The residue was chromatographed on silica with hexane:ethyl acetate (20:7) followed by hexane:ethyl acetate (1:1) to afford the title compound (2.47 g, 43%) as a colourless solid. ¹H NMR (360 MHz, $CDCl_3$) δ 1.94 and 1.99 (3H, 2xd, J=1.3 Hz), 3.72 and 3.75 (3H, 2xs), 4.83 and 4.86 (2H, 2xbr s), 6.20–6.22 and 6.50–6.52 (1H, 2xm), 7.39–7.84 (3H, m), 7.85–7.86 and 8.17–8.18 (1H, 2xm).

Step 3: 2-(3-Aminosulphonylphenyl)propanal

Prepared according to the method of Example 12, Step 2 using 2-(3-aminosulphonylphenyl)-1-methoxypropene. The crude product was used directly without further purification.

Step 4: 4-[3-(5-(1,2,4-Triazol-4-yl)-1H-indol-3-yl)propyl]-1-[2-(3-aminosulphonylphenyl)propyl]piperidine oxalate Prepared according to the method of Example 4, using the compound from Description 2 and 2-(3-aminosulphonylphenyl)propanal. ¹H NMR (360 MHz, $d_6$-DMSO) δ 1.20–1.52 (8H, m), 1.80–1.92 (4H, m), 2.64–2.82 (4H, m), 3.10–3.42 (5H, m), 7.24–7.37 (4H, m), 7.48 (1H, d, J=8.7 Hz), 7.50–7.58 (2H, m), 7.70–7.80 (3H, m), 9.01 (2H, s), 11.09 (1H, br s). MS (ES⁺) 507 (M+1)⁺. Found: C, 54.86; H, 6.35; N, 12.82%. $C_{27}H_{34}N_6O_2S$. $1.4(CO_2H)_2$. $H_2O$ requires: C, 55.00; H, 6.01; N, 12.91%.

EXAMPLE 21

4-[3-(5-(1,2,4-Triazol-4-yl)-1H-indol-3-yl)propyl]-1-[2-(pyrimidin-2-yl)propyl]piperidine. Oxalate Step 1: Diethyl 2-(pyrimidin-2-yl)malonate To a solution of sodium hydride (4.4 g of a 60% dispersion in oil, 0.11 mol) in DMF (200 ml) was added diethyl malonate (16 ml, 0.11 mol) in DMF (50 ml) dropwise at room temperature. After 30 min 2-bromopyrimidine (8.0 g, 0.05 mol) was added portionwise and the solution heated at 100° C. for 3 h. The solution was cooled to room temperature, water (100 ml) was added and the mixture extracted with EtOAc (3×60 ml). The combined organic layers were dried ($MgSO_4$) and evaporated. The residue was chromatographed on silica, using hexane:EtOAc (3:1) as the eluant, to afford the ester (5.9 g, 49%) as a pale yellow oil which solidified on standing at 0° C. ¹H NMR (360 MHz, $CDCl_3$) δ 1.29 (6H, t, J=7.1 Hz), 4.29 (4H, q, J=7.1 Hz), 5.10 (1H, s), 7.26 (1H, t, J=4.9 Hz), 8.74 (2H, d, J=4.9 Hz).

Step 2: Ethyl (pyrimidin-2-yl)acetate

A solution of diethyl 2-(pyrimidin-2-yl)malonate (1.0 g, 4.2 mmol) and sodium chloride (491 mg, 8.4 mmol) in DMSO (6 ml) and water (151 μl, 8.4 mmol) was heated at 180° C. for 20 min. The mixture was cooled to room temperature, water (12 ml) was added, and the solution extracted with EtOAc (2×20 ml). The combined organic layers were dried ($MgSO_4$) and evaporated. The residue was chromatographed on silica, eluting with hexane:EtOAc (2:1), to afford the ester (434 mg, 62%) as a pale yellow oil. ¹H NMR (250 MHz, $CDCl_3$) δ 1.27 (3H, t, J=7.1 Hz), 4.04 (2H, s), 4.23 (2H, q, J=7.1 Hz), 7.22 (1H, t, J=5.3 Hz), 8.72 (2H, d, J=5.3 Hz).

Step 3: Ethyl 2-(pyrimidin-2-yl)propanoate

To a solution of diisopropylamine (2.2 ml, 0.015 mol) in THF (60 ml) at 0° C., was added butyl lithium (9.6 ml of a 1.6 M solution in hexane, 0.015 mol) dropwise. The solution was stirred at 0° C. for 30 min then cooled to −78° C. and iodomethane (960 μl, 0.015 mol) added dropwise. The solution was stirred at −78° C. for 10 min, −50° C. for 30 min then at room temperature for 20 min. After this time $NH_4Cl$ (sat., 30 ml) was added and the mixture stirred at room temperature for 10 min. Water (100 ml) was added and the mixture was extracted with EtOAc (2×100 ml). The combined organic layers were dried ($Na_2SO_4$) and evaporated. The residue was chromatographed on silica, eluting with hexane:EtOAc (2:1), to give the ester (1.8 g, 71%) as a yellow oil. ¹H NMR (250 MHz, $CDCl_3$) δ 1.22 (3H, t, J=7.2 Hz), 1.62 (3H, d, J=7.2 Hz), 4.12 (1H, q, J=7.2 Hz), 4.22 (2H, q, J=7.2 Hz), 7.19 (1H, t, J=4.9 Hz), 8.74 (2H, d, J=4.9 Hz).

Step 4: 2-(Pyrimidin-2-yl)propan-1-ol

To a solution of ethyl 2-(pyrimidin-2-yl)propanoate (1.7 g, 9.4 mmol) in THF (100 ml) at 0° C., was added diisobutylaluminium hydride (23.6 ml of a 1.0 M solution in THF, 23.6 mmol) dropwise. After 3 h $NH_4Cl$ (sat., 30 ml) was added and the mixture stirred at room temperature for 30 min. EtOAc (100 ml) was added and the mixture filtered. The filtrate was dried ($Na_2SO_4$) and evaporated. The residue was chromatographed on silica, eluting with $CH_2Cl_2$:MeOH (95:5), to give the alcohol (562 mg, 43%) as a pale yellow oil. ¹H NMR (360 MHz, $CDCl_3$) δ 1.38 (3H, d, J=7.2 Hz), 3.22–3.31 (1H, m), 3.65 (1H, br s), 3.80–4.05 (2H, m), 7.18 (1H, t, J=4.9 Hz), 8.72 (2H, d, J=4.9 Hz).

Step 5: 2-(Pyrimidin-2-yl)propanal

Prepared according to the method of Example 16, Step 4, using 2-(pyrimidin-2-yl)propan-1-ol. The aldehyde was used directly without further purification.

Step 6: 4-[3-(5-(1,2,4-Triazol-4-yl)-1H-indol-3-yl)propyl]-1-[2-(pyrimidin-2-yl)propyl]piperidine. Oxalate Prepared according to the method of Example 4, using the compound from Description 2 and 2-pyrimidin-2-yl) propanal. ¹H NMR (360 MHz, $d_6$-DMSO) δ 1.16–1.56 (8H, m), 1.61–1.83 (4H, m), 2.54–2.67 (4H, m), 3.00–3.10 (1H, m), 3.12–3.21 (1H, m), 3.23–3.50 (3H, m), 7.21–7.26 (2H, m), 7.34 (1H, t, J=4.8 Hz), 7.46 (1H, d, J=8.5 Hz), 7.69 (1H, s), 8.70 (2H, d, J=4.8 Hz), 8.85 (2H, s), 10.84 (1H, br s). MS (ES$^+$) 430 (M+1)$^+$. Found: C, 58.76; H, 6.56; N, 16.97%. $C_{23}H_{31}N_7 \cdot 1.3(C_2H_2O_4) \cdot H_2O$ requires: C, 58.71; H, 6.36; N, 17.37%.

EXAMPLE 22

4-[3-(5-(1,2,4-Triazol-4-yl)-1H-indol-3-yl)propyl]-1-[2-(thiazol-2-yl)propyl]piperidine Step 1: Ethyl 2-(thiazol-2-yl)acetate Prepared according to the method of Example 21, Step 2 using diethyl 2-(thiazol-2-yl)malonate. $^1$H NMR (360 MHz, CDCl$_3$) δ 1.29 (3H, t, J=7.3Hz), 4.09 (2H, s), 4.22 (2H, q, J=7.3 Hz), 7.32 (1H, d, J=3.5 Hz), 7.75 (1H, d, J=3.5 Hz). MS (ES$^+$) 172 (M+1)$^+$.

Step 2: Ethyl 2-(thiazol-2-yl)propanoate

Prepared according to the method of Example 21, Step 3 using ethyl 2-(thiazol-2-yl)acetate. $^1$H NMR (360 MHz, CDCl$_3$) δ 1.29 (3H, t, J=7.1 Hz), 1.67 (3H, d, J=7.2 Hz), 4.17–4.24 (3H, m), 7.29 (1H, d, J=3.3 Hz), 7.73 (1H, d, J=3.3 Hz). MS (ES$^+$) 186 (M+1)$^+$.

Step 3: 2-(Thiazol-2-yl)propan-1-ol

To a stirred solution of ethyl 2-(thiazol-2-yl)propanoate (418 mg, 2.3 mmol) in ether (15 ml) at –10° C. was added LiAlH$_4$ (2.2 ml of a 1.0M solution in ether, 2.2 mmol) dropwise. After 2 h at –10° C. more LiAlH$_4$ (0.5 ml of a 1.0M solution in ether, 0.5 mmol) was added. After a further 1 h more LiAlH$_4$ (0.5 ml of a 1.0M solution in ether, 0.5 mmol) was added. Stirring was continued for 1 h then Na$_2$SO$_4$ (sat., 3 ml) was added and the mixture stirred at room temperature for 10 min. The mixture was filtered and the filtrate evaporated. The residue was chromatographed on silica, eluting with CH$_2$Cl$_2$:MeOH (95:5), to give the alcohol (266 mg, 82%) as a colourless oil. $^1$H NMR (250 MHz, CDCl$_3$) δ 1.42 (3H, d, J=7.1 Hz), 3.31–3.44 (1H, m), 3.64 (1H, br s), 3.80–3.93 (2H, m), 7.25 (1H, d, J=3.3 Hz), 7.70 (1H, d, J=3.3 Hz).

Step 4: 4-[3-(5-(1,2,4-Triazol-4-yl)-1H-indol-3-yl)propyl]-1-[2-(thiazol-2-yl)propyl]piperidine To a solution of 2-(thiazol-2-yl)propan-1-ol (304 mg, 2.1 mmol) in THF (7 ml) at 0° C., was added triethylamine (319 μl, 2.3 mmol) followed by methanesulphonyl chloride (181 μl, 2.3 mmol). The solution was stirred at 0° C. for 1 h then the mixture was filtered and the filtrate evaporated. The crude mesylate was used directly without further purification.

To a solution of the compound from Description 2 (100 mg, 0.32 mmol) in isopropanol was added the mesylate prepared above (144 mg, 0.65 mmol) and K$_2$CO$_3$ (67 mg, 0.48 mmol). The mixture was heated at reflux for 6 h, after which time more mesylate (144 mg, 10.65 mmol) was added. Heating was continued for a further 6 h after which time the solution was cooled to room temperature and filtered. The filtrate was diluted with CH$_2$Cl$_2$ (20 ml) and washed with water (20 ml). The organic layer was separated and the aqueous phase washed with CH$_2$Cl$_2$ (20 ml). The combined organic layers were dried (Na$_2$SO$_4$) and evaporated. The residue was chromatographed on silica, eluting with CH$_2$Cl$_2$:MeOH:NH$_3$ (90:10:1), to give the product (28 mg, 20%) as a colourless gum. $^1$H NMR (360 MHz, CDCl$_3$) δ 1.17–1.40 (5H, m), 1.40 (3H, d, J=7.0 Hz), 1.60–1.77 (4H, m), 1.85–2.12 (2H, m), 2.53–2.77 (4H, m), 2.80–2.98 (2H, m), 3.33–3.48 (1H, m), 7.10–7.14 (2H, m), 7.22 (1H, d, J=3.2 Hz), 7.46 (1H, d, J=8.3 Hz), 7.53 (1H, d, J=2.0 Hz), 7.66 (1H, d, J=3.3 Hz), 8.48 (2H, s). MS (ES$^+$) 435 (M+1)$^+$. Found: C, 64.34; H, 6.76; N, 18.48%. $C_{24}H_{30}N_6S \cdot 0.7(H_2O)$ requires: C, 64.46; H, 7.08; N, 18.79%.

EXAMPLE 23

4-[3-(5-(1,2,4-Triazol-4-yl)-1H-indol-3-yl)propyl]-1-[2-(pyrazin-2-yl)propyl]piperazine Oxalate Step 1: 1-Methoxy-2-(pyrazin-2-yl)pronene Prepared according to the method of Example 12, Step 1 using 2-acetylpyrazine. $^1$H NMR (250 MHz, CDCl$_3$) δ 2.02 (3H, d, J=1.4 Hz), 3.84 (3H, s), 7.22–7.25 (1H, m), 8.29 (1H, d, J=2.5 Hz), 8.37–8.40 (1H, m), 8.48–8.52 (1H, m).

Step 2: 2-(Pyrazin-2-yl)propanal

Prepared according to the method of Example 12, Step 2, using 1-methoxy-2-(pyrazin-2-yl)propene. The aldehyde was used directly without further purification.

Step 3: 4-[3-(5-(1,2,4-Triazol-4-yl)-1H-indol-3-yl)propyl]-1-[2-(pyrazin-2-yl)propyl]piperazine Oxalate Prepared according to the method of Example 4, using the compound from Description 2 and 2-(pyrazin-2-yl)propanal. $^1$H NMR (360 MHz, d$_6$-DMSO) δ 1.24–1.58 (8H, m), 1.61–1.71 (2H, m), 1.72–1.84 (2H, m), 2.64–2.91 (4H, m), 3.18–3.59 (5H, m), 7.25 (1H, s), 7.29 (1H, d, J=8.6 Hz), 7.47 (1H, d, J=8.6 Hz), 7.75 (1H, s), 8.56 (1H, s), 8.61 (1H, s), 8.68 (1H, s), 9.00 (2H, s), 11.07 (1H, br s). MS (ES$^+$) 430 (M+1)$^+$. Found C, 56.12; H, 6.30; N, 15.07%. $C_{25}H_{31}N_7 \cdot 2.2(C_2H_2O_4) \cdot 0.3(H_2O) \cdot 0.3Et_2O$ requires: C, 56.09; H, 6.00; N, 14.96%.

EXAMPLE 24

4-[3-(5-(1,2,4-Triazol-4-yl)-1H-indol-3-yl)propyl]-1-[2-(imidazol-1-yl)propyl]piperazine Oxalate Step 1: Ethyl 2-(imidazol-1-yl)propanoate A solution of imidazole (5.0 g, 0.074 mol), ethyl 2-bromopropanoate (7.6 ml, 0.06 mol) and K$_2$CO$_3$ (11.2 g, 0.08 mol) in DMF (120 ml) was heated at 90° C. for 2 h. After this time the solution was cooled to room temperature, filtered and the filtrate diluted with EtOAc (200 ml). The mixture was washed with water (2×20 ml) and the organic phase separated. The combined aqueous layers were washed with EtOAc (200 ml) and the combined organic layers washed with brine (200 ml). The organic layer was separated, dried (Na$_2$SO$_4$) and evaporated. The residue was chromatographed on silica, eluting with CH$_2$Cl$_2$:MeOH (95:5), to afford the ester (1.1 g, 9%) as a pale yellow oil. $^1$H NMR (250 MHz, CDCl$_3$) δ 1.26 (3H, t, J=7.1 Hz), 1.75 (3H, d, J=7.3 Hz), 4.20 (2H, q, J=7.1 Hz), 4.85 (1H, q, J=7.3 Hz), 7.02–7.04 (1H, m), 7.08–7.10 (1H, m), 7.58 (1H, s).

Step 2: 2-(Imidazol-1-yl)propan-1-ol

Prepared according to the method of Example 22, Step 3, using ethyl 2-(imidazol-1-yl)propanoate. $^1$H NMR (250 MHz, CDCl$_3$) δ 1.47 (3H, d, J=7.0 Hz), 3.30 (1H, br s), 3.66–3.83 (2H, m), 4.18–4.31 (1H, m), 6.90–6.94 (2H, m), 7.41 (1H, s).

Step 3: 4-[3-(5-(1,2,4-Triazol-4-yl)-1H-indol-3-yl)propyl]-1-[2-(imidazol-1-yl)propyl]piperidine. Oxalate Prepared according to the method of Example 22, Step 4, using 2-(imidazol-1-yl)-propan-1-ol. $^1$H NMR (360 MHz, d$_6$-DMSO) δ 1.07–1.20 (2H, m), 1.21–1.38 (3H, m), 1.41 (3H, d, J=6.7 Hz), 2.18–2.38 (2H, m), 2.64–2.78 (3H, m), 2.79–2.91 (1H, m), 2.93–3.10 (2H, m), 4.66–4.77 (1H, m), 7.20–7.27 (2H, m), 7.29 (1H, dd, J=8.5 and 2.1 Hz), 7.47 (1H, d, J=8.5 Hz), 7.53 (1H, s), 7.75 (1H, d, J=1.9 Hz), 8.34 (1H, s), 9.00 (2H, s), 11.07 (1H, br s). MS (ES$^+$) 418 (M+1)$^+$. Found: C, 55.49; H, 6.48; N, 16.68%. $C_{24}H_{31}N_7 \cdot 1.8(C_2H_2O_4) \cdot 0.9(H_2O)$ requires: C, 55.64; H, 6.16; N, 16.46%.

EXAMPLE 25

4-[3-(5-(1,2,4-Triazol-4-yl)-1H-indol-3-yl)propyl]-1-[2-(pyrazol-1-yl)propyl]piperidine Step 1: Ethyl 2-(pyrazol-1-yl)propanoate Prepared according to the method of Example 24, Step 1, using pyrazole. ¹H NMR (250 MHz, CDCl₃) δ 1.25 (3H, t, J=7.2 Hz), 1.79 (3H, d, J=7.3 Hz), 4.23 (2H, q, J=7.2 Hz), 5.10 (1H, q, J=7.3 Hz), 6.32 (1H, t, J=2.1 Hz), 7.55 (2H, d, J=2.1 Hz). MS (ES⁺) 169 (M+1)⁺.

Step 2: 2-(Pyrazol-1-yl)propan-1-ol

Prepared according to the method of Example 21, Step 4, using ethyl 2-(pyrazol-1-yl)propanoate. ¹H NMR (250 MHz, CDCl₃) δ 1.51 (3H, d, J=6.8 Hz), 3.17 (1H, br s), 3.83–3.92 (2H, m), 4.37–4.46 (1H, m), 6.27 (1H, t, J=2.0 Hz), 7.46 (1H, d, J=2.1 Hz), 7.53 (1H, d, J=1.4 Hz).

Step 3: 2-(Pyrazol-1-yl)propanal

Prepared according to the method of Example 16, Step 4, using 2-(pyrazol-1-yl)propan-1-ol. The aldehyde was used directly without further purification.

Step 4: 4-[3-(5-(1,2,4-Triazol-4-yl)-1H-indol-3-yl)propyl]-1-[2-(pyrazol-1-yl)propyl]piperidine Prepared according to the method of Example 4, using the compound of Description 2 and 2-(pyrazol-1-yl)propanal. ¹H NMR (360 MHz, CDCl₃) δ 1.08–1.37 (4H, m), 1.49 (3H, d, J=6.7 Hz), 1.54–1.78 (5H, m), 1.91–2.03 (2H, m), 2.55–2.65 (2H, m), 2.68–2.78 (4H, m), 4.40–4.50 (1H, m), 6.21 (1H, t, J=2.0 Hz), 7.08–7.16 (2H, m), 7.43 (1H, d, J=2.0 Hz), 7.46 (1H, d, J=8.5 Hz), 7.49 (1H, d, J=1.5 Hz), 7.53 (1H, d, J=1.8 Hz), 8.36 (1H, br s), 8.46 (2H, s). MS (ES⁺) 418 (M+1)⁺. Found: C, 68.54; H, 7.30; N, 23.33%. $C_{24}H_{31}N_7 \cdot 0.1(H_2O)$ requires: C, 68.74; H, 7.50; N, 23.38%.

EXAMPLE 26

4-[3-(5-(1,2,4-Triazol-4-yl)-1H-indol-3-yl)propyl]-1-[2-(pyridin-2-yl)propyl]-piperidine. Oxalate Prepared according to the method of Example 22, Step 4 using the compound from Description 2 and 2-(pyridin-2-yl)propanol. ¹H NMR (360 MHz, d₆-DMSO) δ 1.10–1.56 (8H, m), 1.60–1.74 (2H, m), 1.76–1.84 (2H, m), 2.70 (2H, t, J=7.4 Hz), 2.76–2.96 (2H, m), 3.22–3.56 (5H, m), 7.26–7.32 (3H, m), 7.40 (1H, d, J=7.8 Hz), 7.47 (1H, d, J=8.6 Hz), 7.76–7.82 (2H, m), 8.52–8.56 (1H, m), 9.01 (2H, s), 11.09 (1H, br s). MS (ES⁺) 429 (M+1)⁺. Found: C, 57.16; H, 5.98; N, 13.22%. $C_{26}H_{32}N_6 \cdot 2.1(CO_2H)_2 \cdot 0.9(H_2O)$ requires: C, 57.23; H, 6.04; N, 13.26%.

EXAMPLE 27

4-[3-(5-(1,2,4-Triazol-4-yl)-1H-indol-3-yl)proyyl]-1-[2-(pyridin-3-yl)propyl]piperidine Oxalate Step 1: Ethyl 2-(pyridin-3-yl)propanoate Prepared according to the method of Example 21, Step 3 using ethyl 3-pyridylacetate. ¹H NMR (250 MHz, CDCl₃) δ 1.21 (3H, t, J=10.3 Hz), 1.53 (3H, d, J=10.4 Hz), 3.74 (1H, q, J=10.4 Hz), 4.04–4.23 (2H, m), 7.24–7.29 (1H, m), 7.63–7.69 (1H, m), 8.48–8.57 (2H, m).

Step 2: 2-(Pyridin-3-yl)propanol

Prepared according to the method of Example 22, Step 3 using ethyl 2-(pyridin-3-yl)propanoate. ¹H NMR (250 MHz, CDCl₃) δ 1.31 (3H, d, J=10.1 Hz), 2.05 (1H, br s), 2.91–3.05 (1H, m), 3.75 (2H, d, J=9.6 Hz), 7.25 (1H, dd, J=11.3 and 6.9 Hz), 7.55–7.60 (1H, m), 8.42–8.50 (2H, m).

Step 3: 4-[3-(5-(1,2,4-Triazol-4-yl)-1H-indol-3-yl)pronyl]-1-[2-(pyridin-3-yl)propyl]piperidine Oxalate Prepared according to the method of Example 22, Step 4 using the compound from Description 2 and 2-(pyridin-3-yl)propanol. ¹H NMR (360 MHz, d₆-DMSO) δ 1.20–1.54 (8H, m), 1.60–1.82 (4H, m), 2.64–2.90 (4H, m), 3.22–3.42 (5H, m), 7.24–7.32 (2H, m), 7.36–7.40 (1H, m), 7.47 (1H, d, J=8.6 Hz), 7.72–7.78 (2H, m), 8.46–8.48 (1H, m), 8.55–8.59 (1H, m), 9.00 (2H, s), 11.08 (1H, br s). MS (ES⁺) 429 (M+1)⁺. Found C, 57.07; H, 6.01; N, 12.82%. $C_{26}H_{32}N_6 \cdot 2.2(CO_2H)_2 \cdot 0.8(H_2O)$ requires: C, 56.96; H, 5.98; N, 13.11%.

EXAMPLE 28

4-[3-(5- (1,2,4-Triazol-4-yl)-1H-indol-3-yl)propyl]-1-[2-(pyridin-4-yl)propyl]piperidine Oxalate Prepared according to the method of Example 22, Step 4, using the compound from Description 2 and 2-(pyridin-4-yl)propanol. ¹H NMR (360 MHz, d₆-DMSO) δ 1.10–1.52 (8H, m), 1.60–1.82 (4H, m), 2.64–2.90 (4H, m), 3.20–3.40 (5H, m), 7.24–7.32 (2H, m), 7.36–7.39 (2H, m), 7.47 (1H, d, J=8.6 Hz), 7.84–7.86 (1H, m), 8.50–8.54 (2H, m), 9.00 (2H, s), 11.07 (1H, br s). MS (ES⁺) 429 (M+1)⁺. Found: C, 56.56; H, 6.15; N, 13.00%. $C_{26}H_{32}N_6 \cdot 2(CO_2H)_2 \cdot 1.5(H_2O)$ requires: C, 56.68; H, 6.18; N, 13.22%.

EXAMPLE 29

4-[3-(5-(1,2,4-Triazol-4-yl)-1H-indol-3-yl)propyl]-1-[2-(pyridazin-3-yl)propyl]piperidine Oxalate Step 1: 1-Methoxy-2-(pyridazin-3-yl)propene Prepared according to the method of Example 12, Step 1, using 3-acetylpyridazine. ¹H NMR (360 MHz, CDCl₃) δ 2.15 (3H, d, J=1.3 Hz), 3.78 (3H, s), 6.49 (1H, d, J=1.2 Hz), 7.33 (1H, dd, J=8.8 and 4.8 Hz), 8.16 (1H, dd, J=8.8 and 1.6 Hz), 8.95 (1H, dd, J=4.8 and 1.6 Hz).

Step 2: 2-(Pyridazin-3-yl)propanal

To a solution of 1-methoxy-2-(pyridazin-3-yl)propene (0.26 g, 1.72 mmol) in THF (50 ml) and water (10 ml) under nitrogen at ambient temperature was added mercury(II) acetate (1.66 g, 5.2 mmol). This mixture was stirred at room temperature for 2 hours, and was then poured onto potassium iodide solution (7%, 350 ml) and extracted with toluene (2×50 ml). The combined organic phases were washed with potassium iodide (7%, 140 ml) and brine (90 ml), dried (Na₂SO₄) and evaporated to give the title compound (54 mg, 23%), as an orange gum. The crude aldehyde was used directly without further purification.

Step 3: 4-[3-(5-(1,2,4-Triazol-4-yl)-1H-indol-3-yl)propyl]-1-[2-(pyridazin-3-yl)propyl]piperidine Oxalate Prepared according to the method of Example 4 using the compound from Description 2 and 2-(pyridazin-3-yl) propanal. ¹H NMR (360 MHz, d₆-DMSO) δ 1.20–1.56 (8H, m), 1.62–1.84 (4H, m), 2.64–2.94 (4H, m), 3.30–3.50 (3H, m), 3.60–3.72 (2H, m), 7.24–7.34 (2H, m), 7.48 (1H, d, J=8.6 Hz), 7.68–7.78 (3H, m), 9.01 (2H, s), 9.14–9.18 (1H, m), 11.10 (1H, br s). MS (ES⁺) 430 (M+1)⁺. Found: C, 54.23; H, 5.87; N, 15.42%. $C_{25}H_{31}N_7 \cdot 2.1(CO_2H)_2 \cdot 1.5(H_2O)$ requires: C, 54.32; H, 5.96; N, 15.19%.

DESCRIPTION 4

4-Fluoro-4-[3-(5-(1,2,4-triazol-4-yl)-1H-indol-3-yl)propyl] piperidine a) 4-(Hydroxy)-4'-(1-tert-butyldimethylsilyloxy-4-pentyn-5-yl)-N-(tert-butoxycarbonyl)piperidine 1-tert-Butyldimethylsilyl-4-pentyn-1-ol (4.6 g, 0.028 mmol) was placed in a dry three-neck flask under N₂ and charged with tetrahydrofuran (40 ml) and cooled to −78° C. n-Butyllithium (1.6M in hexanes, 18.8 ml, 0.030 mol) was added dropwise and the solution stirred at −78° C. for 0.5 h. N-tert-Butyloxycarbonyl-4-piperidone (4.0 g, 0.0184 mol) was dissolved in tetrahydrofuran (10 ml) and added dropwise to the lithio anion and the reaction mixture stirred at −78° C. for 0.5 h, and then at 0° C. for another 0.5 h. The reaction was quenched by the slow addition of saturated NH$_4$Cl (40 ml) and extracted with ethyl acetate (3×20 ml). The organic layers were combined, dried over MgSO$_4$ and evaporated. The residue was chromatographed on silica using petroleum ether-ethyl acetate as eluent (9:1→7:3) to give the product as a colourless oil (6.2 g). $^1$H NMR (250 MHz, CDCl$_3$) δ −0.012 (6H, s), 0.84 (9H, s), 1.40 (9H, s), 1.48–1.82 (6H, m), 2.25 (2H, t), 3.16 (2H, m), 3.60–3.77 (4H).

b) 4-Fluoro-4'-(1-tert-butyldimethylsilyloxy-4-pentyn-5-yl)-N-(tert-butoxycarbonyl)piperidine The alcohol from step a (1.5 g, 3.6 mmol) was dissolved in dichloromethane (20 ml) and cooled to −78° C. under N$_2$. Diethylaminosulfur trifluoride (DAST, 1.05 ml, 0.0079 mol) was added dropwise over 10 minutes. The reaction was stirred at −78° C. for 0.5 h and warmed to 0° C. for 20 min. The reaction was slowly poured into cold saturated NaHCO$_3$ (40 ml) and extracted with ethyl acetate (2×20 ml). The organic layers were combined and dried over MgSO$_4$ and evaporated. The residue was chromatographed on silica eluting with petrol:ether (20:1→10:1) to yield the fluoroalkyne as a colourless oil (0.81 g). $^1$H NMR (250 MHz, CDCl$_3$) δ 0.00 (6H, s), 0.83 (9H, s), 1.40 (9H, s), 1.66 (2H, m), 1.61–1.91 (4H, m), 2.28 (2H, m), 3.35–3.55 (4H, m), 3.62 (2H, t).

c) 4-Fluoro-4'-(5-hydroxypentanyl)-N-tert-butoxycarbonylpiperidine

The fluoroalkyne from step b (0.800 g) was dissolved in EtOH (10 ml) and hydrogenated over 10% palladium on carbon at 50 psi for 3 h. The catalyst was filtered and the ethanol removed in vacuo. The residue was dissolved in THF (10 ml) and treated with tetrabutylammonium fluoride (1.0M solution in THF, 9.6 ml) for 16 h. The solvents were removed in vacuo and the residue partitioned between ethyl acetate (40 ml) and H$_2$O (20 ml). The organic layer was dried over MgSO$_4$ and evaporated. The residue was chromatographed on silica eluting with petrol:ethyl acetate (7:30) to yield the alcohol as a colourless oil (0.48 g, 86% yield). $^1$H NMR (250 MHz, CDCl$_3$) δ 1.37–1.45 (6H, m), 1.45 (9H, s), 1.50–1.62 (6H, m), 1.78 (2H, m), 3.06 (2H, m), 3.64 (2H, t), 3.89 (2H, m).

d) 4-Fluoro-4-[3-(5-(1,2,4-triazol-4-yl)-1H-indol-3-yl)propyl]piperidine

The alcohol from step c (1.5 g, 0.0052 mol) was dissolved in dichloromethane (20 ml) and 4 Å molecular sieves (2.5 g) was added, followed by N-methylmorpholine-N-oxide (0.913 g, 0.0078 mol) and tetrapropylammonium perruthenate (0.913 g, 0.26 mmol). The reaction was stirred under N$_2$ for 0.5 h and diluted with ethyl acetate and filtered through a 3" plug of silica. The filtrate was collected and the solvent evaporated in vacuo. The residue was reacted with 4-(1,2,4-triazol-4-yl)phenylhydrazine according to the procedure outlined in Description 2 (step f) to yield 4-fluoro-4-[3-(5-(1,2,4-triazol-4-yl)-1H-indol-3-yl)propyl]piperidine as a colourless foam. $^1$H NMR (250 MHz, CDCl$_3$) δ 1.42–1.92 (8H, m), 2.79 (2H, t), 2.88–2.98 (4H, m), 7.13 (1H, d), 7.16 (2H, d), 7.48 (1H, d), 7.54 (1H, d), 8.37 (2H, s), 8.47 (1H, br s). MS (ES$^+$) (328, M+1).

EXAMPLE 30

4-Fluoro-4-[3-(5-(1,2,4-triazol-4-yl)-1H-indol-3-yl)propyl]-1-[2-(pyridin-3-yl)propyl]piperidine Oxalate Prepared according to the method of Example 22, Step 4 using the compound from Description 4 and 2-(pyridin-3-yl)propanol (Example 27, Step 3). $^1$H NMR (360 MHz, d$_6$-DMSO) δ 1.24 (3H, d, J=6.8 Hz), 1.60–1.90 (8H, m), 2.64–2.78 (4H, m), 2.98–3.26 (5H, m), 7.26–7.38 (3H, m), 7.48 (1H, d, J=8.7 Hz), 7.70–7.80 (2H, m), 8.42–8.46 (1H, m), 8.50–8.54 (1H, m), 9.01 (2H, s), 11.10 (1H, br s). MS (ES$^+$) 447 (M+1)$^+$. Found C, 57.54; H, 6.29; N, 14.13%.

EXAMPLE 31

4-[3-(5-(1,2,4-Triazol-4-yl)-1H-indol-3-yl)proyl]-1-[2-(thien-3-yl)propyl]piperidine Oxalate Step 1: Ethyl 2-(thien-3-yl)propanoate Prepared according to the method of Example 21, Step 3 using ethyl 3-thienylacetate. 1H NMR (360 MHz, CDCl$_3$) δ 1.24 (3H, t, J=7.2 Hz), 1.51 (3H, d, J=7.1 Hz), 3.82 (1H, q, J=7.1 Hz), 4.08–4.19 (2H, m), 7.07 (1H, dd, J=5.1 and 1.1 Hz), 7.11–7.13 (1H, m), 7.27 (1H, dd, J=5.0 and 3.1 Hz).

Step 2: 2-(Thien-3-yl)propanol

Prepared according to the method of Example 22, Step 3 using ethyl 2-(thien-3-yl)propanoate. $^1$H NMR (360 MHz, CDCl$_3$) δ 1.29 (3H, d, J=7.0 Hz), 3.04–3.12 (1H, m), 3.62–3.72 (2H, m), 7.02 (1H, dd, J=5.0 and 1.3 Hz), 7.04–7.07 (1H, m), 7.31 (1H, dd, J=5.0 and 2.9 Hz).

Step 3: 2-(Thien-3-yl)propanal

Prepared according to the method of Example 16, Step 4, using 2-(thien-3-yl)propanol. $^1$H NMR (360 MHz, CDCl$_3$) δ 1.46 (3H, d, J=7.1 Hz), 3.70–3.78 (1H, m), 6.99 (1H, dd, J=5.0 and 1.2 Hz), 7.10–7.13 (1H, m), 7.36 (1H, dd, J=4.9 and 3.0 Hz), 9.65 (1H, d, J=1.7 Hz).

Step 4: 4-[3-(5-(1,2,4-Triazol-4-yl)-1H-indol-3-yl)propyl]-1-[2-(thien-3-yl)propyl]piperidine Oxalate Prepared according to the method of Example 4, using the compound from Description 2 and 2-(thiophen-3-yl)propanal. $^1$H NMR (360 MHz, d$_6$-DMSO) δ 1.10–1.56 (8H, m), 1.62–1.82 (4H, m), 2.64–2.90 (4H, m), 3.10–3.42 (5H, m), 7.13 (1H, d, J=5.0 Hz), 7.24–7.80 (3H, m), 7.46–7.66 (2H, m), 7.74–7.76 (1H, m), 9.00 (2H, s), 11.08 (1H, br s). MS (ES$^+$) 434 (M+1)$^+$. Found: C, 58.76; H, 6.46; N, 11.82%. C$_{25}$H$_{31}$N$_5$S. 1.4(CO$_2$H)$_2$. 0.6(H$_2$O). 0.3(Et$_2$O) requires C, 58.93; H, 6.72; N, 11.49%.

EXAMPLE 32

4-[3-(5-(1,2,4-Triazol-4-yl)-1H-indol-3-yl)propyl]-1-[2-(2-methoxypridin-3-yl)propyl]piperidine Oxalate Step 1: 1-Methoxy-2-(2-methoxypridin-3-yl)propene Prepared according to the method of Example 12, Step 1 using 3-acetyl-2-methoxypyridine. $^1$H NMR (250 MHz, CDCl$_3$) δ 1.86 (3H, d, J=1.3 Hz), 3.72 (3H, s), 3.97 (3H, s), 6.44–6.46 (1H, m), 6.83 (1H, dd, J=7.3 and 5.1 Hz), 7.39 (1H, dd, J=7.3 and 1.8 Hz), 8.01 (1H, dd, J=5.0 and 1.8 Hz).

Step 2: 2-(2-Methoxypyridin-3-yl)propanal

Prepared according to the method of Example 12, Step 2 using 1-methoxy-2-(2-methoxypridin-3-yl)propene. The crude aldehyde was used directly without further purification.

Step 3: 4-[3-(5-(1,2,4-Triazol-4-yl)-1H-indol-3-yl)propyl]-1-[2-(2-methoxypyridin-3-yl)propyl]piperidine Oxalate Prepared according to the method of Example 4, using the compound from Description 2 and 2-(2-methoxypyridin-3-yl)propanal. $^1$H NMR (360 MHz, d$_6$-DMSO) δ 1.20–1.52 (8H, m), 1.60–1.82 (4H, m), 2.60–2.82 (4H, m), 3.00–3.44 (5H, m), 3.89 (3H, s), 6.96–7.01 (1H, m), 7.24–7.32 (2H, m), 7.48 (1H, d, J=8.5 Hz), 7.64–7.70 (1H, m), 7.74–7.78 (1H, m), 8.04–8.10 (1H, m), 9.00 (2H, s), 11.08 (1H, br s). MS (ES$^+$) 459 (M+1)$^+$. Found: C, 60.61; H, 6.74; N, 14.37%. C$_{27}$H$_{34}$N$_6$O 1.3(CO$_2$H)$_2$. 0.5(H$_2$O) requires: C, 60.81; H, 6.48; N, 14.37%.

EXAMPLE 33

4-[3-(5-(1,2,4-Triazol-4-yl)-1H-indol-3-yl)propyl]-1-[2-(4-methoxypyridin-3-yl)propyl]piperidine Oxalate Step 1: 3-Acetyl-4-methoxypyridine A solution of 3-acetyl-4-chloropyridine (0.75 g, 4.8 mmol) in sodium methoxide solution (0.5M in methanol, 10.6 ml, 5.3 mmol) was heated at reflux for 1 hour. After cooling water (10 ml) was added and the solvents evaporated. The residue was partitioned between dichloromethane (4×50 ml) and water (50 ml), the combined organic phases dried (MgSO$_4$) and evaporated to afford the title compound (0.58 g, 80%) as a yellow solid. $^1$H NMR (360 MHz, CDCl$_3$) δ 2.62 (3H, s), 3.98 (3H, s), 6.90 (1H, d, J=5.8 Hz), 8.57 (1H, d, J=5.7 Hz), 8.81 (1H, s).

Step 2: 1-Methoxy-2-(4-methoxypyridin-3-yl)propene

Prepared according to the method of Example 12, Step 1 using 3-acetyl-4-methoxypyridine. $^1$H NMR (250 MHz, CDCl$_3$) δ 1.85 and 1.94 (3H, 2×d, J=1.5 Hz), 3.56 and 3.71 (3H, 2×s), 3.88 (3H, s), 6.10–6.11 and 6.22–6.23 (1H, 2×m), 6.77 and 6.81 (1H, 2×d, J=5.8 Hz), 8.23 and 8.31 (1H, 2×s), 8.35–8.38 (1H, m).

Step 3: 2-(4-Methoxypyridin-3-yl)propanal

Prepared according to the method of Example 12, Step 2 using 1-methoxy-2-(4-methoxypyridin-3-yl)propene. $^1$H NMR (250 MHz, CDCl$_3$) δ 1.45 (3H, d, J=7.1 Hz), 3.77 (1H, q, J=7.2 Hz), 3.88 (3H, s), 6.85 (1H, d, J=5.7 Hz), 8.28 (1H, s), 8.46–8.50 (1H, m), 9.69 (1H, s).

Step 4: 4-[3-(5-(1,2,4-Triazol-4-yl)-1H-indol-3-yl)propyl]-1-[2-(4-methoxypyridin-3-yl)propyl]piperidine Oxalate Prepared according to the method of Example 4, using the compound from Description 2 and 2-(4-methoxypyridin-3-yl)propanal. $^1$H NMR (360 MHz, d$_6$-DMSO) δ 1.18–1.56 (8H, m), 1.60–1.82 (4H, m), 2.60–2.86 (4H, m), 3.10–3.50 (5H, m), 3.87 (3H, s), 7.05 (1H, d, J=2.0 Hz), 7.25–7.32 (2H, m), 7.47 (1H, d, J=5.7 Hz), 7.76 (1H, d, J=8.6 Hz), 8.35–8.39 (2H, m), 9.01 (2H, s), 11.08 (1H, br s). MS (ES$^+$) 459 (M+1)$^+$. Found: C, 56.78; H, 6.82; N, 12.99%. C$_{27}$H$_{34}$N$_6$O. 1.6(CO$_2$H)$_2$. 2(H$_2$O) requires: C, 56.79; H, 6.50; N, 13.15%.

EXAMPLE 34

Chiral separation of the enantiomers of 4-[3-(5-(1,2,4-triazol-4-yl)-1H-indol-3-yl)propryl]-1-[2-pyridin-3-yl)propyl]piperidine 4-[3-(5-(1,2,4-Triazol-4-yl)-1H-indol-3-yl)propyl]-1-[2-(pyridin-3-yl)propyl]piperidine (100 mg, 0.23 mmol) was dissolved in 20% EtOH in hexane (12 mg/ml). 50 μl of solution was injected onto a Chiralpak AS column (250×4.6 mm i.d., 10NM) per run, using 20% EtOH in hexane as the mobile phase. Using a flow rate of 2.5 ml/min and UV detection at 235 nm, the two enantiomers were efficiently separated. The fractions containing each separate enantiomer were combined and evaporated in vacuo.

Peak A (25 mg): Retention time 27.8 min. mp=89° C. (dec.).
Purity A:B>99.5:0.5
Peak B (27 mg): Retention time 17.8 min. mp=92° C. (dec.).
Purity B:A>99.5:0.5.

EXAMPLE 35

(S)-4-[3-(5-(1,2,4-Triazol-4-yl)-1H-indol-3-yl) propyl]-1-(2-phenylnpropyl)piperidine. Bis Hydrochloride a) 5-(N-tert-Butoxycarbonyl-4-piperidinyl)pent-1-yl benzoate The alcohol from Description 2d (116 g, 448 mmol) was dissolved in dry pyridine (1l) and cooled to 0° C. Benzoyl chloride (96 g, 80 ml), 683 mmol) was added, maintaining the internal temperature of the reaction at below 5° C. The reaction was stirred for 16 hours and 3-dimethylaminopropylamine (48 g, 60 ml, 470 mmol) was added and the reaction was stirred for a further 0.5 h, before diluting with ethyl acetate. The organic layer was washed with 10% citric acid solution until the washings were acidic and then the organic layer was washed with brine, saturated aqueous sodium bicarbonate solution, dried (MgSO$_4$), filtered and evaporated to yield an oil which crystallised on standing (168 g). $^1$H NMR (250 MHz, CDCl$_3$) δ 1.45 (9H, s), 0.98–1.84 (13H, m), 2.65 (2H, dt, J=13 and 2.6 Hz), 4.04–4.09 (2H, m), 4.32 (2H, t, J=7.5 Hz), 7.27–7.59 (3H, m), 8.02–8.06 (2H, m).

b) 5-(4-Piperidinyl)-1-pentyl benzoate

The foregoing product (25 g, 67 mmol) was added to trifluoroacetic acid (200 ml) portionwise, at 0° C. The reaction was stirred for one hour and the solution was evaporated and the residue was taken up into ethyl acetate and washed with saturated aqueous sodium bicarbonate until the aqueous washings were alkaline. The organic extract was dried (MgSO$_4$), filtered and evaporated to yield an oil (18.33 g). $^1$H NMR (360 MHz, CDCl$_3$) δ 1.34–1.49 (9H, m), 1.73–1.81 (2H, m), 1.85–1.88 (2H, m), 2.80–2.84 (2H, m), 3.30–3.40 (2H, m), 4.31 (2H, t, J=6.6 Hz), 7.44 (2H, t, J=6.5 Hz), 7.53–7.58 (1H, m), 8.02–8.04 (2H, m).

c) (S)-5-[1-(2-phenylpropyl)piperidin-4-yl]-1-pentanol

The foregoing product (17.4 g, 66.7 mmol) and (S)-2-phenylpropionic acid (10 g, 66.7 mmol) were dissolved in dichloromethane and cooled to 0° C. Triethylamine (185 ml, 133 mmol) and bis(2-oxo-2-oxazolidinyl)phosphinic chloride (17 g, 66.7 mmol) were added and the reaction mixture was stirred for 16 hours. The solvent was removed and the residue was taken up into ethyl acetate and washed with potassium carbonate solution, 10% citric acid solution, water, saturated aqueous sodium bicarbonate solution, and then dried (MgSO$_4$), filtered and evaporated to yield an oil (16.5 g) which was dissolved in borane THF complex (400 ml of a 1M solution in tetrahydrofuran) and heated to reflux for 16 hours. The reaction was cooled, and the solvent was removed. The residue was taken up into acetone (500 ml), 2N hydrochloric acid solution (100 ml) was added and the reaction was stirred for one hour. The acetone was evaporated and the aqueous solution was washed with ethyl acetate, basified with ammonium hydroxide solution and then extracted to dryness to yield an oil which was purified by column chromatography on silica using 10% methanol/dichloromethane as eluant to yield an oil (9.1 g). $^1$H NMR (250 MHz, CDCl$_3$) δ 1.27 (3H, d, J=7 Hz), 1.06–2.00 (14H, m), 2.35–2.51 92H, m), 2.81–3.03 (4H, m), 3.62 (2H, t, J=7.5 Hz), 7.14–7.37 (5H, m).

d) (S)-4-[3-(5-(1,2,4-Triazol-4-yl)-1H-indol-3-yl)-propyl]-1-(2-phenylpropyl)piperidine. Bis Hydrochloride The foregoing product was dissolved in dry dimethylsulfoxide (11 ml) and triethylamine (74.5 g) was added and the reaction mixture was stirred vigorously while adding sulfurtrioxide pyridine in portions for one hour. The mixture was then poured into ice/water and extracted with ethyl acetate. The organic extract was washed with water (3×), dried (MgSO$_4$), filtered and evaporated to yield an oil which was dissolved in ethanol (100 ml) and was added dropwise to a solution of 4-(1,2,4-triazol-4-yl)phenylhydrazine hydrochloride (Description 1) (9.0 g) in 200 ml of 4% sulphuric acid solution at 70° C. over a period of one hour. The reaction was then heated to reflux and was stirred for 16 hours. The reaction was cooled and basified with ammonium hydroxide and extracted with butanol. The organic extract was washed with water and evaporated to yield an oil which was purified by column chromatography on silica eluting with 5% methanol-dichloromethane to give an oil which was converted to the hydrochloride salt. 98.6% e.e. by hplc using a Chiralpak Ad column (250×4.6 mm i.d.) at 40° C. eluting with 5% ethanol in hexane with 0.1% diethylamine at a flow rate of 1 ml/min. $^1$H NMR (250 MHz, DMSO) δ 1.29 (3H, d, J=6.7 Hz), 1.28–1.72 (10H, m), 2.52–3.41 (8H, m), 7.23–7.42 (8H, m) 7.54 (1H, d, J=8.6 Hz), 7.93 (1H, d, J=2 Hz), 9.82 (2H, s), 10.28 (1H, bs), 11.33 (1H, s), MS (ES$^+$) 428 (M+1)$^+$. Found: C, 59.93; H, 7.30; N, 12.85; $C_{27}H_{33}N_5$. 2HCl. 2.25($H_2O$) requires: C, 59.94; H, 7.36; N, 12.94%.

EXAMPLE 36

(R)-4-[3-(5-(1,2,4-Triazol-4-yl)-1H-indol-3-yl) propyl]-1-(2-phenylpropyl)piperidine. Bis Hydrochloride Prepared according to the method of Example 35 using (R)-2-phenylpropionic acid. 98.2% e.e. by h.plc using the methods described in Example 35. MS (ES$^+$) 428 (M+1)$^+$. Found: C, 60.33; H. 7.42; N, 12.99; $C_{27}H_{33}N_5$. 2HCl. 2$H_2O$ requires C, 60.44; H, 7.33; N, 13.05%.

EXAMPLE 37

4-[3-(5-(1,2,4-Triazol-4-yl)-1H-indol-3-yl)propyl]-1-[2-(2-fluorophenyl)propyl]piperidine. Bis Hydrochloride Prepared from 2-fluoroacetophenone according to the method of Example 4. $^1$H NMR (360 MHz, DMSO) δ 1.33 (3H, d, J=7 Hz), 1.28–1.75 (10H, m), 2.85–3.61 (8H, m), 7.17–7.53 (7H, m), 7.88 (1H, d, J=2.2 Hz), 8.24 (1H, s), 8.49 (2H, s); MS (ES$^+$) 446 (M+1)$^+$. Found: C, 56.64; H, 7.04; N, 12.23; $C_{27}H_{32}N_5F$. 2HCl. 3$H_2O$ requires C, 56.93; H, 6.84; N, 12.07%.

EXAMPLE 38

4-[3-(5-(1,2,4-Triazol-4-yl)-1H-indol-3-yl)propyl]-1-[2-(3-fluorophenyl)propyl]piperidine. Bis Hydrochloride Prepared from 3-fluoroacetophenone according to the method of Example 4. $^1$H NMR (250 MHz, DMSO) δ 1.16 (3H, d, J=6.8 Hz), 1.00–2.01 (10H, m), 2.20–3.10 (8H, m), 6.90–7.08 (3H, m), 7.20–7.33 (3H, m), 7.46 (1H, d, J=8.5 Hz), 7.76 (1H, d, J=2 Hz), 9.02 (2H, s), 11.06 (1H, s); MS (ES$^+$) 446 (M+1)$^+$. Found: C, 56.74; H, 5.87; N, 10.62; $C_{27}H_{32}N_5F$. 2($CO_2H)_2$. 1.5($H_2O$) requires: C, 57.03; H, 6.03; N, 10.73%.

EXAMPLE 39

4-[3-(5-(1,2,4-Triazol-4-yl)-1H-indol-3-yl)propyl]-1-[2-(4-fluorophenyl)propyl]piperidine. Bis Hydrochloride Prepared from 4-fluoroacetophenone according to the method of Example 4. $^1$H NMR (360 MHz, DMSO) δ 1.27 (3H, d, J=6.9 Hz), 1.28–1.80 (10H, m), 2.60–3.45 (8H, m), 7.15–7.20 (2H, m), 7.20 (1H, d, J=1 Hz), 7.35–7.42 (3H, m), 7.52 (1H, d, 8.6 Hz), 7.86 (1H, d, J=1 Hz), 9.55 (2H, s), 11.22 (1H, s); MS (ES$^+$) 446 (M+1)$^+$. Found: C, 55.39; H, 6.89; N, 12.04; $C_{27}H_{32}N_5F$. 2HCl. 3½$H_2O$ requires: C, 55.84; H, 7.12; N, 12.07%.

EXAMPLE 40

4-[3-(5-(1,2,4-Triazol-4-yl)-1H-indol-3-yl)propyl]-1-[2-(2-chloro-5-(trifluoromethyl)phenyl)propyl] piperidine. Bis Hydrochloride Prepared from 2-chloro-5-(trifluoromethyl)acetophenone according to the method of Example 4. $^1$H NMR (360 MHz, CDCl$_3$) δ 1.27 (3H, d, J=6.8 Hz), 1.05–1.38 (6H, m), 1.60–1.80 (3H, m), 1.90–2.06 (2H, m), 2.40–2.58 (2H, m), 2.73 (2H, t, J=7.5 Hz), 2.70–2.84 (1H, m), 2.96–3.00 (1H, m), 3.52–3.60 (1H, m); MS (ES$^+$) 531 (M+1)$^+$.

DESCRIPTION 5

(S)-2-(4-Fluorophenyl)propionic acid a) (R)-4-Benzyl-(R and S)-3-[2-(4-fluorophenyl) propionamido]-2-oxazolidinone (R)-(+)-4-benzyl-2-oxazolidinone (9.0 g, 50.8 mmol) in dry tetrahydrofuran (250 ml) was cooled to −78° C. and butyllithium (32 ml of 1.6M in hexane, 50.8 mmol) was added dropwise to the solution maintaining the temperature below −70° C. After 0.5 hours (R,S)-2-(4-fluorophenyl) propionyl chloride (8.6 g, 46.2 mmol) in tetrahydrofuran (10 ml) was added below −70° C. and the reaction was stirred for 0.5 h. Saturated ammonium chloride was added and the reaction was extracted with ethyl acetate, dried (MgSO$_4$), filtered and evaporated. The two diastereomers were separated by column chromatography on silica using ethyl acetate/hexane (1:4) to yield the less polar diastereomer tentatively assigned as (R)-4-benzyl-(R)-3-[2-(4-fluorophenyl)propionamido]-2-oxazolidinone (7.5 g); and the more polar isomer, tentatively assigned as (R)-4-benzyl-(S)-3-[2-(4-fluorophenyl)propionamido]-2-oxazolidinone (6.5 g).

b) (S)-2-(4-Fluorophenyl)propionic acid

The more polar diastereomer obtained from step a (silica, ethyl acetate/hexane (1:4)) (6.5 g, 19.2 mmol) was dissolved in tetrahydrofuran/water (4:1) (100 ml) and cooled to 0° C. Hydrogen peroxide (30% aqueous solution, 7.9 ml, 77 mmol) was added dropwise below 5° C., followed by lithium hydroxide (0.74 g, 31.0 mmol). The reaction was allowed to warm to 20° C. over 1.5 hours and then quenched ith sodium sulfite (12.6 g) in water (75 ml). The reaction was washed ith dichloromethane (×3) and the aqueous was acidified to pH 1 at 0° C. with hydrochloric acid and then extracted with ethyl acetate (3×) and the organic extract was dried (MgSO$_4$), filtered, and evaporated to yield an oil, which crystallised on standing (3.11 g). $^1$H NMR (250 MHz, DMSO) δ 1.35 (3H, d, J=7.1 Hz), 3.70 (1H, q, J=7.1 Hz), 7.10–7.19 (2H, m), 7.29–7.36 (2H, m); [α]$^{20}$D CHCl$_3$ (C=1.2)=+57.1°

EXAMPLE 41

(S)-4-[3-(5-(1,2,4-Triazol-4-yl)-1H-indol-3-yl) propyl]-1-[2-(4-fluorophenyl)propyl]piperidine. Bis Hydrochloride Prepared according to the method of Example 35 Step c using (S)-2-(4-fluorophenyl)propionic acid. Obtained in >99.5% e.e. by hplc. $^1$H NMR (360 MHz, DMSO) δ 1.28 (3H, d, J=6.8 Hz), 1.29–1.80 (1H, m), 2.60–3.45 (8H, m), 7.16–7.20 (2H, m), 7.20 (1H, d, J=1 Hz), 7.35–7.41 (3H, m), 7.53 (1H, d, J=8.8 Hz), 7.88 (1H, d, J=1 Hz), 9.59 (2H, s), 9.99 (1H, bs), 11.23 (1H, s); MS (ES$^+$) 446 (M+1)$^+$.

EXAMPLE 42

4-[3-(5-(1 2,4-Triazol-4-yl)-1H-indol-3-yl)propyl]-1-(2-hydroxy-2-phenylpropyl)piperidine α-Methyl styrene epoxide (Org. Prep. Proced. Int., 1989, 757–761) (0.26 g, 2 mmol) and the product of Description 2 (0.309 g, 1 mmol) were heated to 100° C. in methanol (5 ml) in a sealed tube for 16 hours. The solvent was removed and the residue was purified by silica chromatography eluting with 2-propanol/dichloromethane (1:20) with 0.1% ammonium hydroxide. The pure fractions were converted to the hydrochloride salt (0.065 g). $^1$H NMR (250 MHz, DMSO) δ 1.63 (3H, s), 1.20–1.80 (9H, m), 2.69–3.62 (8H, m), 7.25–7.59 (8H, m), 7.95 (1H, d, J=2 Hz), 9.95 (2H, s), 11.39 (1H, s); MS (ES$^+$) 444 (M+1)$^+$. Found: C, 54.56; H, 6.81; N, 11.55; $C_{27}H_{33}N_5O$. 3HCl. 2.5($H_2O$) requires: C, 54.34; H, 6.93; N, 11.74%.

EXAMPLE 43

4-[3-(5-(N-(Methyl)aminosulphonylmethyl)-1H-indol-3-yl)propyl]-1-(2-phenylpropyl)piperidine Hydrochloride Prepared from 4-(N-(methyl)aminosulphonylmethyl)-phenylhydrazine hydrochloride (DE 3320521) using the method of Description 2f. $^1$H NMR (250 MHz, DMSO) δ 1.28 (3H, d, J=6.3 Hz), 1.26–1.76 (10H, m), 2.52 (3H, d, J=6 Hz), 2.62–3.60 (8H, m), 4.34 (2H, s), 6.78–6.84 (1H, m), 7.04–7.36 (8H, m), 7.48 (1H, s), 9.60–9.80 (1H, bs), 10.86 (1H, s), MS (ES$^+$) 468 (M+1)$^+$. Found: C, 62.58; H, 7.66; N, 8.22. $C_{27}H_{37}N_3O_2S$. HCl. 0.75($H_2O$) requires: C, 62.58; H, 7.69; N, 8.12%.

EXAMPLE 44

4-[3-(5-(N-(Methyl)aminosulphonylethyl)-1H-indol-3-yl)propyl]-1-(2p-henylpropyl)piperidine Hydrochloride Prepared from 4-(N-(methyl)aminosulphonylethyl)phenylhydrazine hydrochloride using the method of Description 2f. $^1$H NMR (250 MHz, DMSO) δ 1.28 (3H, d, J=6.4 Hz), 1.27–1.78 (10H, m), 2.61 (3H, d, J=5 Hz), 2.60–3.42 (12H, m), 6.94–7.36 (10H, m), 9.65–9.75 (1H, bs), 10.72 (1H, s); MS (ES$^+$) 482 (M+1)$^+$. Found: C, 63.46; H, 7.92; N, 7.87; $C_{28}H_{39}N_3O_2S$. HCl. 0.75($H_2O$) requires C, 63.26; H, 7.87; N, 7.90%.

EXAMPLE 45

4-[3-(5-(2-Ethylimidazol-1-yl)-1H-indol-3-yl)propyl]-1-(2-phenylpropyl)piperidine Hydrochloride Prepared from 4-(2-ethylimidazol-1-yl)phenylhydrazine using the method of Description 2f which was in turn prepared from 4-(2-ethylimidazol-1-yl)aniline (BE 880020) using the method of Description 1(d). $^1$H NMR (500 MHz, DMSO+trifluoroacetic acid) δ 1.17 (3H, t, J=7.6 Hz), 1.26 (3H, d, J=5.5 Hz), 1.15–1.78 (10H, m), 2.67 (2H, t, J=7.2 Hz) 2.83 (2H, q, J=7.5 Hz), 2.74–3.46 (6H, m), 7.19–7.26 (2H, m), 7.33 (1H, s), 7.78 (1H, s), 7.82 (1H, d, J=2 Hz), 11.28 (1H, s); MS (ES$^+$) 455 (M+1)$^+$; Found: C, 64.11; H, 7.73; N, 9.96. $C_{30}H_{38}N_4$. 2HCl. 2$H_2O$ requires C, 63.93 H, 7.87; N, 9.94%.

EXAMPLE 46

4-[3-(5-((S)-2-Oxo-1,3-oxazolidin-4-ylmethyl)-1H-indol-3-yl)propyl]-1-(2-phenylpropyl)piperidine Hydrochloride a) 4-[3-(5-((S)-2-Oxo-1,3-oxazolidin-4-ylmethyl)-1H-indol-3-yl)propyl]piperidine Hydrochloride (S)-4-(4-Hydrazinobenzyl)-1,3-oxazolid-2-one hydrochloride (J. Med. Chem., 1995, 38(18), 3566–3580) (0.8 g) and the product of Description 2(e) (1 g) were dissolved in acetic acid (10 ml), water (30 ml) and ethanol (15 ml) and heated at 60° C. for one hour and then at reflux for 16 hours. The reaction was cooled and then evaporated and the residue basified with ammonium hydroxide and extracted with butanol. The organic phase was washed with water and evaporated and used unpurified for the next step.

b) 4-[3-(5-((S)-2-Oxo-1,3-oxazolidin-4-ylmethyl)-1H-indol-3-yl)propyl]-1-[(R,S)-2-phenylpropyl]piperidine Hydrochloride Prepared from the foregoing product using the method of Example 4. $^1$H NMR (250 MHz, DMSO) δ 1.28 (3H, d, J=6.3 Hz), 1.29–1.80 (10H, m), 2.50–2.86 and 3.27–3.60 (10H, m), 3.98–4.15 (2H, m), 4.16–4.28 (1H, m), 6.92 (1H, dd, J=2 and 7.5 Hz), 7.05 (1H, d, J=2 Hz), 7.24 (1H, d, J=8 Hz), 7.23–7.37 (5H, m), 7.79 (1H, s), 9.50–9.65 (1H, bs), 10.71 (1H, s); MS (ES$^+$) 460 (M+1)$^+$. Found: C, 66.73; H, 7.65; N, 7.97. $C_{29}H_{37}N_3O$. HCl. 1.5($H_2O$) requires: C, 66.58; H, 7.90; N, 8.03%.

EXAMPLE 47

4-Fluoro-4-[3-(5-(1,2,4-Triazol-4-yl)-1H-indol-3-yl)propyl]-1-(2-phenylpropyl)piperidine oxalate Prepared according to the method of Example 4 using the compound from Description 4 and (±)-2-phenylpropionaldehyde. $^1$H NMR (DMSO, 360 MHz) δ 1.28 (3H, d), 1.66–1.70 (4H, m), 1.94 (4H, m), 2.73 (2H, t), 2.97 (2H, m), 3.32 (2H, m), 7.24–7.35 (7H), 7.47 (1H, d), 7.78 (1H, d), 9.01 (2H, s), 11.12 (1H, br s). MS (ES$^+$) (446, M+1).

EXAMPLE 48

4-[2-Fluoro-3-(5-(1,2,4-triazol-4-yl)-1H-indol-3-yl)propyl]-1-(2-phenyl-propyl)piperidine oxalate a) 3-[N-[(tert-butyloxy)carbonyl]piperidinyl-4-yl]-1,2-porpylene oxide To sodium hydride (1.2 g, 0.03 mol of a 60% dispersion in oil) and trimethylsulfoxonium iodide (6.6 g, 0.03 mol) at 0° C. under $N_2$ was added anhydrous DMSO dropwise. The ice-bath was removed after complete addition and the reaction stirred at 25° C. for 30 min. The reaction was then cooled to 0° C., and a solution of 2-[N-[(tert-butyloxy)carbonyl]piperidin-4-yl]ethyl aldehyde (prepared according to J. Med. Chem., 1994, 37, 2537–2551) (6.8 g, 0.03 mol) was added in a steady stream as a solution in anhydrous DMSO (15 ml). The ice-bath was removed, the reaction stirred at 25° C. for 15 min and then at 50° C. for 1h. The reaction mixture was cooled, quenched with $H_2O$ (40 ml) then poured into $H_2O$ (100 ml) and ethyl acetate (50 ml). The reaction mixture was extracted with ethyl acetate (2×) and the organic layer washed with $H_2O$ (3×20ml). The combined organic extracts were dried over $MgSO_4$, evaporated and the residue chromatographed on silica eluting with ethyl acetate: petrol (10:90 to 20:80) to obtain the epoxide as a colourless oil (4.7 g, 49% yield). $^1$H NMR (250 MHz, $CDCl_3$) 6 1.14–1.28 (3H, m), 1.45 (9H, s), 1.63–1.78 (4H, m), 2.44 (1H, dd), 2.71 (2H, t), 2.77 (1H, t), 2.95 (1H, m), 4.12 (2H, m).

b) (±)-5-[N-(tert-Butyloxycarbonyl)piperidin-4-yl]-4-hydroxy-1-triethylsilyl-1-pentyne A dry flask under $N_2$ was charged with THF (50 ml) and n-butyllithium (13 ml, 0.021 mol, 1.6 M solution in hexanes) and cooled to −78° C. Triethylsilylacetylene (3.0 ml, 0.021 mol) was added dropwise and the reaction stirred for 0.5 h. Distilled boron trifluoride etherate (3.03 ml, 0.025 mol) was then added and the reaction stirred at −78° C. for a further 10 min. The epoxide (step a) was then added as a solution in THF (20 ml) and the reaction stirred for 0.75 h. The reaction was quenched by the addition of saturated NH$_4$Cl and extracted into ethyl acetate. The organic layer was dried over MgSO$_4$ and evaporated in vacuo. The residue was taken up in dioxane:water (1:1, 100 ml) and triethylamine (2.0 ml, 0.0145 mol) added followed by tert-butyldicarbonate (3.0 g, 0.0145 mol). The reaction was stirred for 1h, the dioxane evaporated and the residue partitioned between ethyl acetate and saturated NH$_4$Cl. The organic layer was collected, dried over MgSO$_4$ and evaporated. The residue was chromatographed on silica eluting with ethyl acetate:hexanes (1:9→2:8) to obtain the alcohol as a colourless oil (2.4 g, 49%). $^1$H NMR (250 MHz, CDCl$_3$) δ 0.58 (6H, q), 0.95 (9H, t), 1.08–1.16 (3H, m), 1.45 (9H, s), 1.59–1.78 (4H, m), 2.35 (1H, dd), 2.47 (1H, dd), 2.73 (2H, t), 4.12 (3H, m).

c) (±)-5-[N-(tert-Butyloxycarbonyl)piperidin-4-yl]-4-fluoro-1-triethylsilyl-1-pentyne The alcohol from step b (1.0 g, 0.003 mol) was dissolved in CH$_2$Cl$_2$ and cooled to −78° C. Diethylaminosulfurtrifluoride (0.8 ml, 0.0057 mol) was added dropwise and the reaction was stirred at −78° C. for 15 min and warmed to 0° C. over 0.5 h. The reaction was quenched by pouring into cold saturated NaHCO$_3$ (20 ml) and extracted into ethyl acetate (2×20 ml). The organic layers were combined, washed with brine, dried over MgSO$_4$ and evaporated. The residue was chromatographed on silica eluting with petroleum ether:ether (20:1) to obtain the fluoride as a colourless oil (0.250 g, 22%). $^1$H NMR (250 MHz, CDCl$_3$) δ 0.59 (6H, q), 0.96 (9H, t), 1.08–1.28 (3H, m), 1.64–1.78 (4H, m), 2.47–2.75 (4H, m), 4.12 (2H, m), 4.60 (0.5H, m), 4.81 (0.5H, m).

d) (±)-4-[2-Fluoro-3-(5-(1,2,4-triazol-4-yl)-1H-indol-3-yl)propyl]-N-(tert-butyloxycarbonyl)piperidine The fluoroalkyne from step c (0.250 g, 0.652 mmol) was dissolved in anhydrous DMF (10 ml) and 2-iodo-4-(1,2,4-triazol-4-yl)aniline (0.186 g, 0.652 mmol) was added, together with sodium carbonate (0.276 g, 2.6 mmol), magnesium sulfate (0.090 g, 0.72 mmol) and anhydrous lithium chloride (0.028 g, 0.652 mmol). The reaction mixture was de-gassed using a stream of N$_2$ for 10 min and palladium acetate (0.016 g, 0.071 mmol) added. After de-gassing the reaction for a further 5 min, the reaction was heated at 105° C. for 16 h. The reaction mixture was cooled, the DMF removed in vacuo and the residue partitioned between butanol/water. The organic layer was collected, dried over MgSO$^4$ and evaporated. The crude residue was dissolved in MeOH (10 ml) and 5M HCI (6 ml) and the reaction stirred at 25° C. for 72 h. The solvents were removed in vacuo and the residue dissolved in dioxane:water (1:1, 10 ml) and basified to pH 9 with solid K$_2$CO$_3$. Di-tert-butyldicarbonate (0.285 g, 1.3 mmol) was then added and the reaction stirred for 12 h. The reaction mixture was partitioned between 5% MeOH/EtOAc and H$_2$O, the organic layer collected, dried over MgSO$^4$ and evaporated. The residue was chromatographed on silica eluting with a gradient consisting of CH$_2$Cl$_2$ then 1–5% MeOH:CH$_2$Cl$_2$ to obtain the product as a colourless oil (0.120 g, 43%). $^1$H NMR (250 MHz, CDCl$_3$) δ 1.09–1.16 (3H, m), 1.44 (9H, s), 1.63-1.74 (4H, m), 2.70 (2H, m), 3.02 (1H, t), 3.09 (1H, d), 4.12 (2H, m), 4.79 (0.5H, m), 4.94 (0.5H, m), 7.15 (1H, dd), 7.25 (2H, d), 7.50 (1H, d), 7.58 (1H, s), 8.48 (2H, s), 8.63 (1H, br s).

e) 4-[2-Fluoro-3-(5-(1,2,4-triazol-4-yl)-1H-indol-3-yl)propyl]-1-(2-phenylpropyl)piperidine oxalate The compound from step d (0.120 g) was treated with trifluoroacetic acid (3 ml) and the excess acid removed in vacuo. The residue was dissolved in MeOH (5 ml) and sodium methoxide (0.165 g) added. The resulting amine was reacted with (±)-2-phenylpropionaldehyde according to the procedure described for Example 4 to obtain the title compound as a pale yellow solid. $^1$H NMR (free base, 250 MHz, CDCl$_3$) δ 1.26 (3H, d), 1.30–2.20 (10H, m), 2.49 (2H, d), 2.90–3.00 (3H, m), 3.08 (1H, d), 4.73 (0.5H, m), 4.93 (0.5H, m), 7.13–7.31 (7H, m), 7.48 (1H, d), 7.56 (1H, d), 8.34 (2H, s), 8.46 (1H, br s). Oxalate salt MS (ES$^+$) (446, M+1).

EXAMPLE 49

4-[3-(5-(1,2,4-Triazol-4-yl)-1H-indol-3-yl)-2-hydroxypropyl]-1-(2-phenylpropyl)piperidine oxalate a) 4-[3-(5-(1,2,4-Triazol-4-yl)-1H-indol-3-yl)-2-hydroxypropyl]-N-(tert-butyloxycarbonyl)piperidine Prepared according to the procedure described for Example 49 step d, using (±)-5-[N-(tert-butyloxycarbonyl)piperidin-4-yl]-4-hydroxy-1-triethylsilyl-1-pentyne (Example 49, step b) and 2-iodo-4-(1,2,4-triazol-4-yl)aniline. $^1$H NMR (250 MHz, CDCl$_3$) δ 1.04–1.19 (3H, m), 1.44 (9H, s), 1.68 (4H, m), 2.69 (2H, bt), 2.82 (1H, dd), 3.0 (1H, dd), 4.08 (3H, m), 7.17 (1H, dd), 7.25 (2H, m), 7.50 (1H, d), 7.59 (1H, d), 8.44 (2H, s), 8.46 (1H, s).

b) 4-[3-(5-(1,2,4-Triazol-4-yl)-1H-indol-3-yl)-2-hydroxypropyll-1-(2-phenylpronyl)pileridine oxalate Prepared according to the procedure described for Example 48, step e, using the product from step a, and (±)-2-phenylpropionaldehyde. $^1$H NMR (360 MHz, DMSO) δ 1.26 (3H, d), 1.27–1.44 (4H, m), 1.74 (3H, m), 2.68 (2H, m), 2.80 (2H, d), 3.07–3.20 (5H, m), 3.86 (1H, m), 7.24–7.35 (7H, m), 7.47 (1H, d), 7.74 (1H, d), 8.85 (2H, s), 10.89 (1H, br s). MS (ES$^+$) (444, M+1) Found: C, 58.98%; H, 6.35%; N, 11.16%. C$_{27}$H$_{34}$N$_5$O. 2(C$_2$H$_2$O$_4$). 0.5H$_2$O requires C, 58.78%; H, 6.20%; N, 11.05%.

EXAMPLE 50

4-13-(5-(1,2,4-Triazol-4-yl)-1H-indol-3-yl)-2-oxopropyl]-1-(2-phenylpropyl)piperidine hydrochloride Prepared according to the procedure described in Description 2, step e, using the compound from Example 49, step b, and sulfur trioxide pyridine complex. $^1$H NMR (free base, 250 MHz, CDCl$_3$) δ 1.23 (3H, d), 1.58 (3H, d), 1.83–1.88 (4H, m), 2.42 (5H, m), 2.78–3.00 (2H, m), 3.81 (2H, s), 7.17–7.30 (7H, m), 7.48 (1H, d), 7.52 (1H, d), 8.46 (2H, s), 8.70 (1H, br s).

EXAMPLE 51

4-[3-(5-(1,2,4-Triazol-4-yl)-1H-indol-3-yl)-1-hydroxypropyl]-(2-phenylpropyl)piperidine hydrochloride a) (N-tert-Butoxycarbonylpiperidin-4-yl)-4-keto-diethylmethylphosphonate Diethylmethylphosphonate (4.96 g, 32.6 mmol) was dissolved in tetrahydrofuran (60 ml) and cooled to −78° C. n-BuLi (1.6M solution in hexanes, 20.3 ml, 32.6 mmol) was added dropwise and the reaction stirred under N$_2$ for 1 h. Ethyl (N-tert-butoxycarbonyl)isonipecotate (3 g, 13.0 mmol) in THF (2 ml) was added dropwise and the reaction stirred at −78° C. for 0.5 h. The reaction was quenched with saturated NH$_4$Cl and extracted with ethyl acetate (3×). The combined organic layers were dried over MgSO$^4$ and concentrated in vacuo. The residue was chromatographed on silica eluting with ethyl acetate:hexanes (1:1) to obtain the product as a colourless oil (0.530 g). $^1$H NMR (250 MHz, CDCl$_3$) δ 1.33 (6H, t), 1.44 (9H, s), 1.51 (4H, m), 1.70 (2H, m), 2.70–2.82 (3H, m), 3.13 (2H, d), 4.02–4.20 (4H, m).

b) 4-[3-(5-(1,2,4-Triazol-4-yl)-1H-indol-3-yl)-1-hydroxypropyl]-N-(tert-butoxycarbonyl)piperidine (i) Sodium hydride (0.084 g, 2.083 mmol, 60% dispersion in oil) was dissolved in anhydrous DMF (5 ml) under N$_2$ and cooled to 0° C. (N-tert-Butoxycarbonylpiperldin-4-yl)-4-keto-diethylmethylphosphonate (step a, 0.530 g, 1.5 mmol) in DMF (3 ml) was added dropwise and the reaction stirred for 1 h. 5-(1,2,4-Triazol-4-yl)-1-(N-p-toluenesulfonyl)-indole-3-carboxaldehyde (0.500 g, 1.37 mmol) in hot DMF (5 ml) was then added and the reaction stirred at 25° C. for 16 h. The reaction was quenched by the addition of water (30 ml) and extracted with ethyl acetate (2×). The organic layer was washed with water (3×) and dried over MgSO$^4$ and concentrated in vacuo. The residue was purified on silica eluting with CH$_2$Cl$_2$, then 1–3% MeOH/CH$_2$Cl$_2$ to give 0.300 g of a colourless oil.

(ii) The compound from above was hydrogenated over freshly prepared Wilkinson's catalyst (0.025 g) in 5 ml of ethyl acetate for 16 h. The solvent was removed and the residue dissolved in ethanol (10 ml) and cooled to 0° C. Sodium borohydride (0.0368 g) was added and the reaction stirred at 0° C. for 1 h. The solvent was removed and the reaction partitioned between n-butanol/water. The organic layer was evaporated and the residue chromatographed on silica eluting with CH$_2$Cl$_2$, then 1–10% MeOH/CH$_2$Cl2 to obtain 0.212 g of a colourless oil.

c) 4-[3-(5-(1,2,4-Triazol-4-yl)-1H-indol-3-yl)-1-hydroxypropyl]-1-(2-phenylpropyl)piperidine hydrochloride Prepared according to the method described for Example 48, step e using the compound from above (step b) and (±)-2-phenylpropionaldehyde. The resulting compound was refluxed with KOH (0.034 g) in MeOH (5 ml) for 16 h. The compound was purified by preparative thin layer chromatography. $^1$H NMR (360 MHz, DMSO) δ 1.27 (3H, d), 1.40 (1H, m), 1.42–1.90 (9H, m), 2.73 (2H, m), 2.87 (2H, m), 3.26 (2H, m), 3.38 (1H, m). MS (ES$^+$) (445, M+1).

We claim:

1. A compound of formula I, or a salt or prodrug thereof:

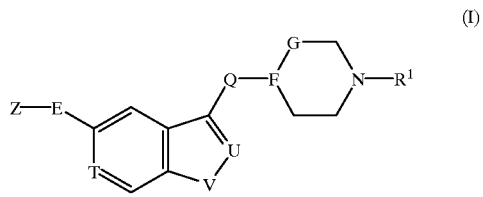

(I)

wherein

Z represents —SO2NR$^5$R$^6$ or a group of formula (Zb):

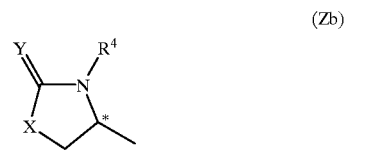

(Zb)

in which the asterisk * denotes a chiral centre; or
Z represents an optionally substituted imidazol-1-yl; 1,2,4-triazol-1-yl; or 1,2,4-triazol-4-yl moiety, the optional substituents being one or more groups selected from methyl, ethyl, benzyl, and amino;
X represents oxygen;
Y represents oxygen;
E represents a chemical bond or a methylene or ethylene linkage;
Q represents a straight propylene chain, optionally substituted in any position by one or more substituents selected from fluoro and hydroxy, or by an oxo moiety;
T represents CH;
U represents C-R$^2$;
V represents N-R$^3$;
-F-G- represents —CM=CH$_2$— or —C=CH—;
M represents hydrogen, halogen or C$_{1-6}$ alkoxy;
R$^1$ represents C$_{3-6}$ alkyl, C$_{3-6}$ alkenyl, C$_{3-6}$ alkynyl, C$_{3-7}$ cycloalkyl(C$_{1-6}$)alkyl, aryl(C$_{1-6}$)alkyl or heteroaryl(C$_{1-6}$)alkyl, any of which groups may be optionally substituted;
R$^2$ and R$^3$ both represent hydrogen;
R$^4$ represents hydrogen or methyl; and
R$^5$ and R$^6$ independently represent hydrogen or methyl.

2. A compound as claimed in claim 1 wherein Q represents a straight propylene chain, optionally substituted in any position by one or more substituents selected from fluoro and hydroxy.

3. A compound as claimed in claim 1 represented by formula IIA, and salts and prodrugs thereof:

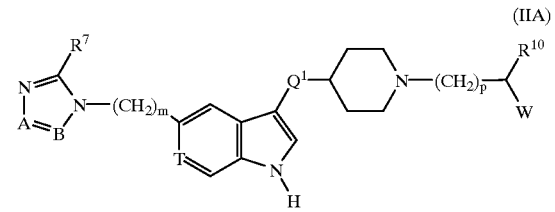

(IIA)

wherein m is zero, 1; or 2;

p is zero, 1 or 2;

Q$^1$ represents a straight propylene chain, optionally substituted in any position by one or more substituents selected from fluoro and hydroxy;

T represents CH;

A represents nitrogen or CH;

B represents nitrogen or C-R$^8$, with the proviso that both A and B cannot simultaneously represent nitrogen;

R$^7$ and R$^8$ independently represent hydrogen, methyl, ethyl, benzyl, or amino;

W represents tert-butyl, cyclohexyl, phenyl, thienyl, thiazolyl, pyrazolyl, imidazolyl, pyridinyl, pyridazinyl, pyrimidinyl or pyridazinyl, any of which groups may be unsubstituted or substituted by one or more groups selected from halogen, cyano, trifluoromethyl, triazolyl, tetrazolyl, C$_{1-6}$ alkyl-tetrazolyl, C$_{1-6}$ alkoxy, C$_{2-6}$ alkylcarbonyl, amino, C$_{1-6}$ alkylamino, di(C$_{1-6}$)alkylamino, di(C$_{1-6}$)alkylaminomethyl, C$_{2-6}$ alkylcarbonylamino, C$_{1-6}$ alkylsulphonylamino, aminocarbonylamino, C$_{1-6}$ alkylaminocarbonyl, arninosulphonyl and C$_{1-6}$ alkylaminosulphonylmethyl; and R$_{10}$ represents hydrogen, C$_{1-3}$ alkyl, hydroxy(C$_{1-3}$)alkyl or C$_{1-6}$ alkylaminocarbonyl.

4. A compound of formula IIB, and salts and prodrugs thereof:

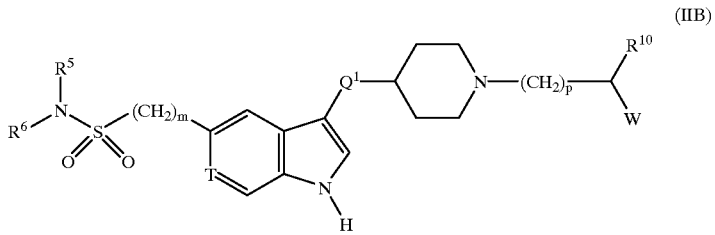

wherein
- m is zero, 1 or 2;
- p is zero, 1 or 2;
- $Q^1$ represents a straight propylene chain, optionally substituted in any position by one or more substituents selected from fluoro and hydroxy;
- T represents CH;
- $R^5$ and $R^6$ represent hydrogen or methyl;
- W represents tert-butyl, cyclohexyl, phenyl, thienyl, thiazolyl, pyrazolyl, imidazolyl, pyridinyl, pyridazinyl, pyrimidinyl or pyridazinyl, any of which groups may be unsubstituted or substituted by one or more groups selected from halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di($C_{1-6}$)alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl and $C_{1-6}$ alkylaminosulphonylmethyl; and
- $R_{10}$ represents hydrogen, $C_{1-3}$ akyl hydroxy($C_{1-3}$)alkyl or $C_{1-6}$ alkylaminocarbonyl.

5. A compound of formula IIC, and salts and prodrugs thereof:

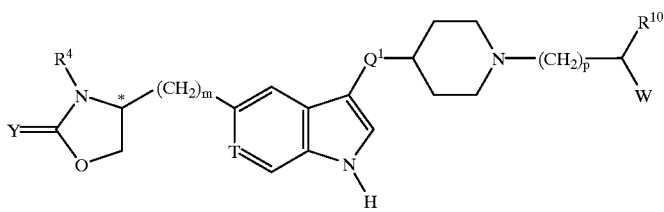

wherein the asterisk * denotes a chiral centre;

m, p, $Q^1$, T, W and $R^{10}$ are as defined in claim 4;

$R^4$ represents hydrogen or methyl; and

Y represents oxygen.

6. A compound as claimed in claim 3 wherein W represents tert-butyl, cyclohexyl or a group of formula (Wa), (Wb) or (Wc):

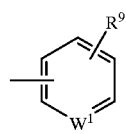

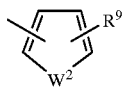

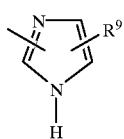

in which
- $W^1$ represents CH or nitrogen;
- $W^2$ represents oxygen, sulphur, NH or N-methyl; and
- $R^9$ represents hydrogen, halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di($C_{1-6}$)alkylamino, di($_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl.

7. A compound selected from:

1-benzyl-4-[3-(5-(1,2,4-triazol-4-yl)-1H-indol-3-yl)propyl]piperidine;
1-(3,3-dimethylbutyl)-4-[3-(5-(1,2,4-triazol-4-yl)-1H-indol-3-yl)propyl]piperidine;
1-(2-phenylethyl)-4-[3-(5-(1,2,4-triazol-4-yl)-1H-indol-3-yl)propyl]piperidine;
1-cyclohexylmethyl-4-[3-(5-(1,2,4-triazol-4-yl)-1H-indol-3-yl)propyl]piperidine;
1-(3-phenylpropyl)-4-[3-(5-(1,2,4-triazol-4-yl)-1H-indol-3-yl)propyl]piperidine;
1-[2-(3-fluorophenyl)ethyl]-4-[3-(5-(1,2,4-triazol-4-yl)-1H-indol-3-yl)propyl]piperidine;
1-[2-(4-trifluoromethylphenyl)ethyl]-4-[3-(5-(1,2,4-triazol-4-yl)-1H-indol-3-yl)propyl]piperidine;
1-[2-(3,4-difluorophenyl)ethyl]-4-[3-(5-(1,2,4-triazol-4-yl)-1H-indol-3-yl)propyl]piperidine;
N-methyl-2-phenyl-2-[4-(3-(5-(1,2,4-triazol-4-yl)-1H-indol-3-yl)propyl)piperidin-1-yl]acetamide;

1-(2-oxo-2-phenylethyl)-4-[3-(5-(1,2,4-triazol-4-yl)-1H-indol-3-yl)propyl]piperidine;
1-(2-phenylpropyl)-4-[3-(5-(1,2,4-triazol-4-yl)-1H-indol-3-yl)propyl]piperidine;
1-(2-hydroxy-1-phenylethyl)-4-[3-(5-(1,2,4-triazol-4-yl)-1H-indol-3-yl)propyl]piperidine;
1-[2-(2-fluorophenyl)ethyl] -4-[3-(5-(1,2,4-triazol-4-yl)-1H-indol-3-yl)propyl]piperidine;
and salts and prodrugs thereof.

8. A compound selected from:
4-[3-(5-(1,2,4-triazol-4-yl)-1H-indol-3-yl)propyl]-1-[2-(2-chlorophenyl)propyl]piperidine;
4-[3-(5-(1,2,4-triazol-4-yl)-1H-indol-3-yl)propyl]-1-[2-(2-trifluoromethylphenyl)propyl]piperidine;
4-[3-(5-(1,2,4-triazol-4-yl)-1H-indol-3-yl)propyl]-1-[2-(4-chlorophenyl)propyl]piperidine;
4-[3-(5-(1,2,4-triazol-4-yl)-1H-indol-3-yl)propyl]-1-[2-(4-methoxyphenyl)propyl]piperidine;
4-[3-(5-(1,2,4-triazol-4-yl)-1H-indol-3-yl)propyl]-1-[2-(2,6-dichlorophenyl)propyl]piperidine;
4-[3-(5-(1,2,4-triazol-4-yl)-1H-indol-3-yl)propyl]-1-[2-(3-methoxyphenyl)propyl]piperidine;
4-[3-(5-(1,2,4-triazol-4-yl)-1H-indol-3-yl)propyl]-1-[2-(2-methoxyphenyl)propyl]piperidine;
4-[3-(5-(1,2,4-triazol-4-yl)-1H-indol-3-yl)propyl]-1-[2-(3-chlorophenyl)propyl]piperidine;
4-[3-(5-(1,2,4-triazol-4-yl)-1H-indol-3-yl)propyl]-1-[2-(3-aminosulphonylphenyl)propyl]piperidine;
4-[3-(5-(1,2,4-triazol-4-yl)-1H-indol-3-yl)propyl]-1-[2-(pyrimidin-2-yl)propyl]piperidine;
4-[3-(5-(1,2,4-triazol-4-yl)-1H-indol-3-yl)propyl]-1-[2-(thiazol-2-yl)propyl]piperidine;
4-[3-(5-(1,2,4-triazol-4-yl)-1H-indol-3-yl)propyl]-1-[2-(pyrazin-2-yl)propyl]piperazine;
4-[3-(5-(1,2,4-triazol-4-yl)-1H-indol-3-yl)propyl]-1-[2-(imidazol-1-yl)propyl]piperazine;
4-[3-(5-(1,2,4-triazol-4-yl)-1H-indol-3-yl)propyl]-1-[2-(pyrazol-1-yl)propyl]piperidine;
4-[3-(5-(1,2,4-triazol-4-yl)-1H-indol-3-yl)propyl]-1-[2-(pyridin-2-yl)propyl]piperidine;
4-[3-(5-(1,2,4-triazol-4-yl)-1H-indol-3-yl)propyl]-1-[2-(pyridin-3-yl)propyl]piperidine;
4-[3-(5-(1,2,4-triazol-4-yl)-1H-indol-3-yl)propyl]-1-[2-(pyridin-4-yl)propyl]piperidine;
4-[3-(5-(1,2,4-triazol-4-yl)-1H-indol-3-yl)propyl]-1-[2-(pyridazin-3-yl)propyl]piperidine;
4-fluoro-4-[3-(5-(1, 2, 4-triazol-4-yl)-1H-indol-3-yl)propyl]-1-[2-(pyridin-3-yl)propyl]piperidine;
4-[$^3$-($^5$-(1,2,4-triazol-4-yl)-1H-indol-3-yl)propyl]-1-[2-(thien-3-yl)propyl]piperidine;
4-[$^3$-(5-(1,2,4-triazol-4-yl)-1H-indol-3-yl)propyl]-1-[2-(2-methoxypyridin-3-yl)propyl]piperidine;
4-[3-(5-(1,2,4-triazol-4-yl)-1H-indol-3-yl)propyl]-1-[2-(4-methoxypyridin-3-yl)propyl]piperidine;
4-[3-(5-(1,2,4-triazol-4-yl)-1H-indol-3-yl)propyl]-1-[(R)-2-(pyridin-3-yl)propyl]piperidine;
4-[3-(5-(1,2,4-triazol-4-yl)-1H-indol-3-yl)propyl]-1-[(S)-2-(pyridin-3-yl)propyl]piperidine;
4-[3-(5-(1,2,4-triazol-4-yl)-1H-indol-3-yl)propyl]-1-[(S)-(2-phenylpropyl]piperidine;
4-[3-(5-(1,2,4-triazol-4-yl)-1H-indol-3-yl)propyl]-1-[(R)-2-phenylpropyl]piperidine;
4-[3-(5-(1,2,4-triazol-4-yl)-1H-indol-3-yl)propyl]-1-[2-(2-fluorophenyl)propyl]piperidine;
4-[3-(5-(1,2,4-triazol-4-yl)-1H-indol-3-yl)propyl]-1-[2-(3-fluorophenyl)propyl]piperidine;
4-[3-(5-(1,2,4-triazol-4-yl)-1H-indol-3-yl)propyl]-1-[2-(4-fluorophenyl)propyl]piperidine;
4-[3-(5-(1,2,4-triazol-4-yl)-1H-indol-3-yl)propyl]-1-[2-(2-chloro-5-(trifluoromethyl)phenyl)propyl]piperidine;
4-[3-(5-(1,2,4-triazol-4-yl)-1H-indol-3-yl)propyl]-1-[(S)-2-(4-fluorophenyl)propyl]piperidine;
4-[3-(5-(1,2,4-triazol-4-yl)-1H-indol-3-yl)propyl]-1-(2-hydroxy-2-phenylpropyl)piperidine;
4-[3-(5-(N-(methyl)aminosulphonylmethyl)-1 H-indol-3-yl)propyl]-1-(2-phenylpropyl)piperidine;
4-[3-(5-(N-(methyl)aminosulphonylethyl)-1H-indol-3-yl)propyl]-1-(2-phenylpropyl)piperidine;
4-[3-(5-(2-ethylimidazol-1-yl)-1H-indol-3-yl)propyl]-1-(2-phenylpropyl)piperidine;
4-[3-(5-((S)-2-oxo-1,3-oxazolidin-4-ylmethyl)-1H-indol-3-yl)propyl]-1-(2-phenylpropyl)piperidine;
4-fluoro-4-[3-(5-(1,2,4-triazol-4-yl)-1H-indol-3-yl)propyl]-1-(2-phenylpropyl)piperidine;
4-[2-fluoro-3-(5-(1,2,4-triazol-4-yl)-1H-indol-3-yl)propyl]-1-(2-phenylpropyl)piperidine;
4-[$^3$-($^5$-(1,2,4-triazol-4-yl)-1H-indol-3-yl)-2-hydroxypropyl]-1-(2-phenylpropyl)piperidine;
4-[3-(5-(1,2,4-triazol-4-yl)-1H-indol-3-yl)-2-oxopropyl]-1-(2-phenylpropyl)piperidine;
4-[3-(5-(1,2,4-triazol-4-yl)-1H-indol-3-yl)-1-hydroxypropyl]-1-(2-phenylpropyl)piperidine;
and salts and prodrugs thereof.

9. A pharmaceutical composition comprising a compound of formula I as defined in claim 1 or a pharmaceutically acceptable salt thereof or a prodrug thereof in association with a pharmaceutically acceptable carrier.

10. A method for the treatment of clinical conditions for which an agonist of 5-HT$_{1D}$ receptors selective for the 5-HT$_{1D_\alpha}$ subtype thereof is indicated, which method comprises administering to a patient in need of such treatment an effective amount of a compound of formula I as defined in claim 1, or a pharmaceutically acceptable salt thereof or a prodrug thereof.

11. A compound as claimed in claim 4 wherein W represents tert-butyl, cyclohexyl or a group of formula (Wa), (Wb) or (Wc):

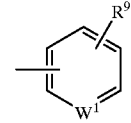

(Wa)

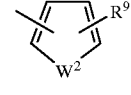

(Wb)

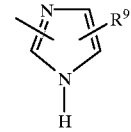

(Wc)

in which
W$^1$ represents CH or nitrogen;
W$^2$ represents oxygen, sulphur, NH or N-methyl; and
R$^9$ represents hydrogen, halogen, cyano, trofluoromethyl, triazolyl, tetrazolyl, C$_{1-6}$ alkyl-tetrazolyl, C$_{1-6}$ alkoxy, C$_{2-6}$ alkylcarbonyl, amino, C$_{1-6}$ alkylamino, di(C$_{1-6}$)alkylamino, di(C$_{1-6}$)alkylaminomethyl, C$_{2-6}$ alkylcarbonylamino, C$_{1-6}$ alkylsulphonylamino, aminocarbonylamino, C$_{1-6}$ alkylaminocarbonyl, aminosulphonyl or C$_{1-6}$ alkylaminosulphonylmethyl.

12. A compound as claimed in claim 5 wherein W represents tert-butyl, cyclohexyl or a group of formula (Wa), (Wb) or (Wc):

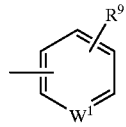
(Wa)

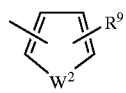
(Wb)

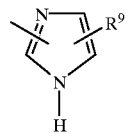
(Wc)

in which
W$^1$ represents CH or nitrogen;
W$^2$ represents oxygen, sulphur, NH or N-methyl; and
W9 repreents hydrogen, halogen, cyano, trifluoromethyl, triazolyl, tetrazolyl, C$_{1-6}$ alkyl-tetrazolyl, C$_{1-6}$ alkoxy, C$_{2-6}$ alkylcarbonyl, amino, C$_{1-6}$ alkylamino, di(C$_{1-6}$)alkylamino, di(C$_{1-6}$)alkylaminomethyl, C$_{2-6}$ alkylcarbonylamino, C$_{1-6}$ alkylsulphonylamino, aminocarbonylamino, C$_{1-6}$ alkylaminocarbonyl, aminosulphonyl or C$_{1-6}$ alkylaminosulphonylmethyl.

* * * * *